(12) United States Patent
Baldwin et al.

(10) Patent No.: US 9,855,318 B2
(45) Date of Patent: Jan. 2, 2018

(54) FUSION PROTEINS

(71) Applicant: Eli Lilly and Company, Indianapolis, IN (US)

(72) Inventors: David Bruce Baldwin, Carmel, IN (US); John Michael Beals, Indianapolis, IN (US); Jonathan Wesley Day, Carmel, IN (US); Craig Duane Dickinson, San Diego, CA (US); Andrew Ihor Korytko, Oceanside, CA (US); Gregory Alan Lazar, Pacifica, CA (US)

(73) Assignee: Eli Lilly and Company, Indianapolis, IN (US)

(*) Notice: Subject to any disclaimer, the term of this patent is extended or adjusted under 35 U.S.C. 154(b) by 0 days.

(21) Appl. No.: 15/140,519

(22) Filed: Apr. 28, 2016

(65) Prior Publication Data
US 2016/0324932 A1 Nov. 10, 2016

Related U.S. Application Data

(60) Provisional application No. 62/158,079, filed on May 7, 2015.

(51) Int. Cl.
| | |
|---|---|
| A61K 38/00 | (2006.01) |
| A61K 39/00 | (2006.01) |
| A61K 38/28 | (2006.01) |
| C07K 14/62 | (2006.01) |
| A61K 38/16 | (2006.01) |
| A61K 38/26 | (2006.01) |
| C07K 14/00 | (2006.01) |

(52) U.S. Cl.
CPC .............. *A61K 38/28* (2013.01); *A61K 38/16* (2013.01); *A61K 38/26* (2013.01); *C07K 14/001* (2013.01); *C07K 14/62* (2013.01); *A61K 38/00* (2013.01); *C07K 2319/30* (2013.01)

(58) Field of Classification Search
CPC ............................ C07K 14/001; C07K 14/62
See application file for complete search history.

(56) References Cited

U.S. PATENT DOCUMENTS

| | | |
|---|---|---|
| 5,424,286 A | 6/1995 | Eng |
| 5,514,646 A | 5/1996 | Chance |
| 6,268,343 B1 | 7/2001 | Knudsen et al. |

(Continued)

FOREIGN PATENT DOCUMENTS

| | | |
|---|---|---|
| CN | 103509118 | 1/2014 |
| KR | 101324828 | 12/2011 |

(Continued)

OTHER PUBLICATIONS

Hua, Q., et al., "Mini-Proinsulin and Mini-IGF-I: Homologous Protein Sequences Encoding Non-Homologous Structures," J. Mol. Biol., 277, pp. 103-118 (1998).

(Continued)

*Primary Examiner* — Cherie M Stanfield
(74) *Attorney, Agent, or Firm* — Matthew T. Lord

(57) ABSTRACT

The present invention relates to fusion proteins comprising an insulin receptor agonist fused to a human IgG Fc region through the use of a peptide linker, and the use of such fusion proteins in the treatment of diabetes. The fusion protein of the present invention has an extended time action profile and is useful for providing basal glucose control for an extended period of time.

4 Claims, 2 Drawing Sheets

(56) References Cited

U.S. PATENT DOCUMENTS

Figure 1:
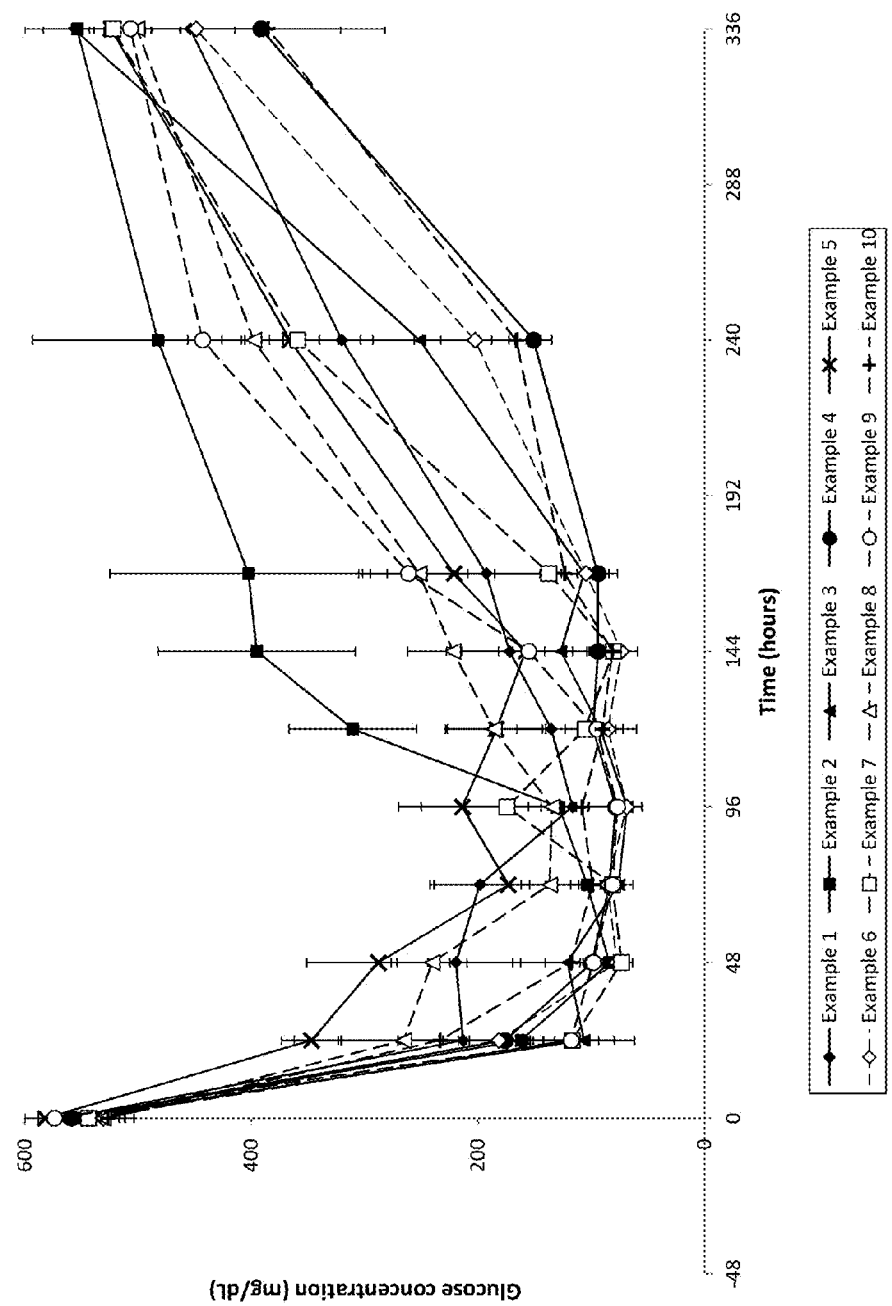

| | | |
|---|---|---|
| 6,630,348 B1 | 10/2003 | Lee et al. |
| 7,271,149 B2 | 9/2007 | Glaesner et al. |
| 7,323,543 B2 | 1/2008 | Van Antwerp et al. |
| 7,452,966 B2 | 11/2008 | Glaesner et al. |
| 8,501,440 B2 | 8/2013 | Weiss |
| 8,883,449 B2 | 11/2014 | Kjeldsen et al. |
| 9,018,161 B2 | 4/2015 | Nielsen et al. |
| 9,260,501 B2 | 2/2016 | Hoeg-Jensen et al. |
| 9,260,502 B2 | 2/2016 | Nielsen et al. |
| 2005/0014679 A1 | 1/2005 | Beals et al. |
| 2009/0069215 A1 | 3/2009 | Madsen et al. |
| 2009/0099065 A1 | 4/2009 | Madsen et al. |
| 2010/0196405 A1 | 8/2010 | Ng |
| 2010/0216690 A1 | 8/2010 | Madsen et al. |
| 2011/0009314 A1 | 1/2011 | Naver et al. |
| 2011/0195896 A1 | 8/2011 | Weiss et al. |
| 2011/0230401 A1 | 9/2011 | Artymiuk et al. |
| 2013/0028918 A1 | 1/2013 | Song et al. |
| 2014/0044717 A1 | 2/2014 | Kranz et al. |
| 2014/0120120 A1 | 5/2014 | Woo et al. |
| 2015/0111820 A1 | 4/2015 | Pridal et al. |
| 2015/0148520 A1 | 5/2015 | DiMarchi et al. |
| 2015/0190528 A1 | 7/2015 | Lim et al. |
| 2015/0196643 A1 | 7/2015 | Lim et al. |
| 2015/0274802 A1 | 10/2015 | DiMarchi et al. |
| 2015/0274803 A1 | 10/2015 | Weiss |
| 2016/0000931 A1 | 1/2016 | Jang et al. |
| 2016/0051696 A1 | 2/2016 | Song et al. |

FOREIGN PATENT DOCUMENTS

| | | |
|---|---|---|
| KR | 110134210 | 12/2011 |
| WO | 9634882 | 11/1996 |
| WO | 2015052088 | 4/2015 |
| WO | 2015108398 | 7/2015 |
| WO | 2015183038 | 12/2015 |
| WO | 2015183054 | 12/2015 |
| WO | 2015199511 | 12/2015 |
| WO | 2016006963 | 1/2016 |
| WO | 2016057529 | 4/2016 |
| WO | 2016081670 | 5/2016 |
| WO | 2016133372 | 8/2016 |

OTHER PUBLICATIONS

Hua, Q., et al. "Design of an Active Ultrastable Single-chain Insulin Analog," J. Biol. Chem., vol. 283, No. 21, pp. 14703-14716 (2008).

Hwang, S.Y., et al., "A Novel Very Long-Acting Insulin Analog (HM12470) with Potential for Once-Weekly Dosing, Has a Favorable PK, PD and Mitogenic Profile," poster presented at the American Diabetes Association 74th Scientific Sessions, San Francisco, CA, Jun. 13-17, 2014.

Park, Y., et al., "Pharmacokinetics and Pharmacodynamics of Ultra-Long Acting Insulin (LAPS-Insulin) in Animal Models," poster presented at the 72nd Scientific Sessions, American Diabetes Association, Philadelphia, PA, Jun. 8-12, 2012.

Kaur, Z., et al., "Discovery of High Potency, Single-Chain Insulin Analogs with a Shortened B-Chain and Nonpeptide Linker," ACS Chem. Biol., vol. 8, pp. 1822-1829 (2013).

Kohn, W., et al., "pI-shifted Insulin Analogs with Extended In Vivo Time Action and Favorable Receptor Selectivity," Peptides, vol. 28 pp. 935-948 (2007).

Kristensen, C., et al. "A Single-Chain Insulin-Like Growth Factor I/insulin Hybrid Binds with High Affinity to the Insulin Receptor," Biochem. J., vol. 305 pp. 981-986 (1995).

Schnellenberger, V., et al., "A Recombinant Polypeptide Extends the in vivo Half-Life of Peptides and Proteins in a Tunable Manner," Nature Biotechnology, vol. 27, No. 12, (2009).

Patent Cooperation Treaty International Search Report and Written Opinion of the International Searching Authority pertaining to International Application No. PCT/US2016/029807; dated Jun. 28, 2016.

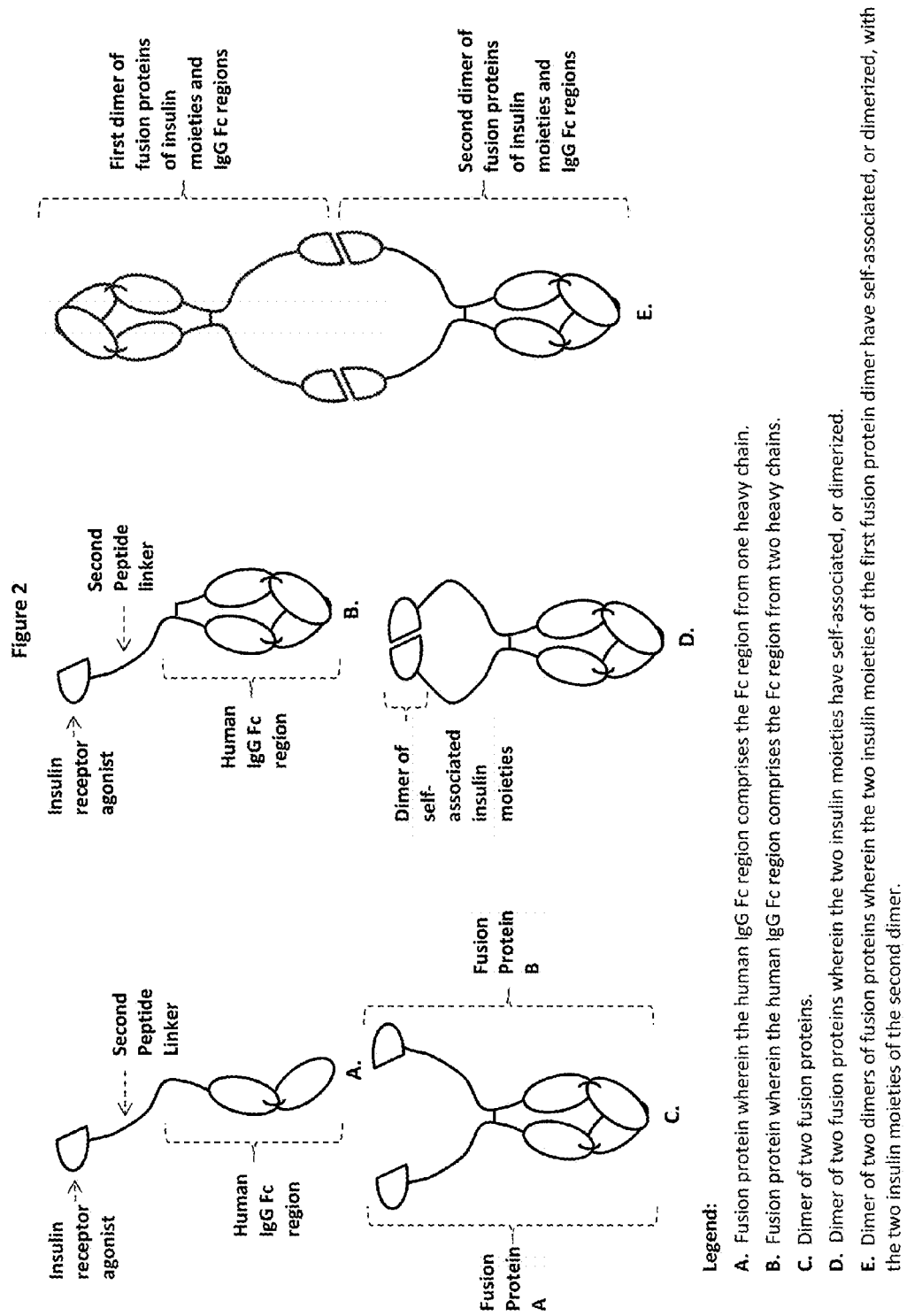

```
                          SEQUENCE LISTING

<160> NUMBER OF SEQ ID NOS: 26

<210> SEQ ID NO 1
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is Phe, Gln or Ala
<220> FEATURE:
<221> NAME/KEY: MISC_FEATURE
<222> LOCATION: (2)..(2)
<223> OTHER INFORMATION: Xaa at position 2 is Val or Gly
<220> FEATURE:
<221> NAME/KEY: MISC_FEATURE
<222> LOCATION: (3)..(3)
<223> OTHER INFORMATION: Xaa at position 3 is Asn, Lys, Asp, Gly, Gln,
      Ala or Glu
<220> FEATURE:
<221> NAME/KEY: MISC_FEATURE
<222> LOCATION: (16)..(16)
<223> OTHER INFORMATION: Xaa at position 16 is Glu, Tyr, Gln or His
<220> FEATURE:
<221> NAME/KEY: MISC_FEATURE
<222> LOCATION: (25)..(25)
<223> OTHER INFORMATION: Xaa at position 25 is His or Phe
<220> FEATURE:
<221> NAME/KEY: MISC_FEATURE
<222> LOCATION: (27)..(27)
<223> OTHER INFORMATION: Xaa at position 27 is Gly, Thr, Ser, His, Val,
      or is absent
```

```
<220> FEATURE:
<221> NAME/KEY: MISC_FEATURE
<222> LOCATION: (28)..(28)
<223> OTHER INFORMATION: Xaa at position 28 is Gly, Glu, Pro, Lys, Asp,
      Ser, His, or is absent
<220> FEATURE:
<221> NAME/KEY: MISC_FEATURE
<222> LOCATION: (29)..(29)
<223> OTHER INFORMATION: Xaa at position 29 is Gly, Glu, Lys, Pro, Gln,
      Asp, His, or is absent
<220> FEATURE:
<221> NAME/KEY: MISC_FEATURE
<222> LOCATION: (30)..(30)
<223> OTHER INFORMATION: Xaa at position 30 is Gly, Thr, Ser, Glu, Lys,
      Ala, or is absent

<400> SEQUENCE: 1

Xaa Xaa Xaa Gln His Leu Cys Gly Ser His Leu Val Glu Ala Leu Xaa
1               5                   10                  15

Leu Val Cys Gly Glu Arg Gly Phe Xaa Tyr Xaa Xaa Xaa Xaa
            20                  25                  30

<210> SEQ ID NO 2
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa at position 10 is Thr or Ile
<220> FEATURE:
<221> NAME/KEY: MISC_FEATURE
<222> LOCATION: (14)..(14)
<223> OTHER INFORMATION: Xaa at position 14 is Asp, Tyr, Gln or Glu
<220> FEATURE:
<221> NAME/KEY: MISC_FEATURE
<222> LOCATION: (21)..(21)
<223> OTHER INFORMATION: Xaa at position 21 is Gly, Asn, Ser, or Ala
<220> FEATURE:
<221> NAME/KEY: MISC_FEATURE
<222> LOCATION: (22)..(22)
<223> OTHER INFORMATION: Xaa at position 22 is any naturally occurring
      amino acid, or is absent

<400> SEQUENCE: 2

Gly Ile Val Glu Gln Cys Cys Thr Ser Xaa Cys Ser Leu Xaa Gln Leu
1               5                   10                  15

Glu Asn Tyr Cys Xaa Xaa
            20

<210> SEQ ID NO 3
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is Gly or is absent
<220> FEATURE:
<221> NAME/KEY: MISC_FEATURE
<222> LOCATION: (3)..(3)
<223> OTHER INFORMATION: Xaa at position 3 is Gly, Ser, or is absent

<400> SEQUENCE: 3

Xaa Gly Xaa Gly Gly Gly Gly
1               5
```

```
<210> SEQ ID NO 4
<211> LENGTH: 59
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is Phe, Gln, or Ala
<220> FEATURE:
<221> NAME/KEY: MISC_FEATURE
<222> LOCATION: (2)..(2)
<223> OTHER INFORMATION: Xaa at position 2 is Val or Gly
<220> FEATURE:
<221> NAME/KEY: MISC_FEATURE
<222> LOCATION: (3)..(3)
<223> OTHER INFORMATION: Xaa at position 3 is Asn, Lys, Asp, Gly, Gln,
      Ala, or Glu
<220> FEATURE:
<221> NAME/KEY: MISC_FEATURE
<222> LOCATION: (16)..(16)
<223> OTHER INFORMATION: Xaa at position 16 is Glu, Tyr, Gln, or His
<220> FEATURE:
<221> NAME/KEY: MISC_FEATURE
<222> LOCATION: (25)..(25)
<223> OTHER INFORMATION: Xaa at position 25 is His or Phe
<220> FEATURE:
<221> NAME/KEY: MISC_FEATURE
<222> LOCATION: (27)..(27)
<223> OTHER INFORMATION: Xaa at position 27 is Gly, Thr, Ser, His, Val,
      or is absent
<220> FEATURE:
<221> NAME/KEY: MISC_FEATURE
<222> LOCATION: (28)..(28)
<223> OTHER INFORMATION: Xaa at position 28 is Gly, Glu, Pro, Lys, Asp,
      Ser, His, or is absent
<220> FEATURE:
<221> NAME/KEY: MISC_FEATURE
<222> LOCATION: (29)..(29)
<223> OTHER INFORMATION: Xaa at position 29 is Gly, Glu, Lys, Pro, Gln,
      Asp, His, or is absent
<220> FEATURE:
<221> NAME/KEY: MISC_FEATURE
<222> LOCATION: (30)..(30)
<223> OTHER INFORMATION: Xaa at position 30 is Gly, Thr, Ser, Glu, Lys,
      Ala, or is absent
<220> FEATURE:
<221> NAME/KEY: MISC_FEATURE
<222> LOCATION: (31)..(31)
<223> OTHER INFORMATION: Xaa at position 31 is Gly or is absent
<220> FEATURE:
<221> NAME/KEY: MISC_FEATURE
<222> LOCATION: (33)..(33)
<223> OTHER INFORMATION: Xaa at position 33 is Gly, Ser, or is absent
<220> FEATURE:
<221> NAME/KEY: MISC_FEATURE
<222> LOCATION: (47)..(47)
<223> OTHER INFORMATION: Xaa at position 47 is Thr or Ile
<220> FEATURE:
<221> NAME/KEY: MISC_FEATURE
<222> LOCATION: (51)..(51)
<223> OTHER INFORMATION: Xaa at position 51 is Asp, Tyr, Gln, or Glu
<220> FEATURE:
<221> NAME/KEY: MISC_FEATURE
<222> LOCATION: (58)..(58)
<223> OTHER INFORMATION: Xaa at position 58 is Gly, Asn, Ser, or Ala
<220> FEATURE:
<221> NAME/KEY: MISC_FEATURE
<222> LOCATION: (59)..(59)
<223> OTHER INFORMATION: Xaa at position 59 is any naturally occurring
      amino acid, or is absent

<400> SEQUENCE: 4

Xaa Xaa Xaa Gln His Leu Cys Gly Ser His Leu Val Glu Ala Leu Xaa
1               5                   10                  15

Leu Val Cys Gly Glu Arg Gly Phe Xaa Tyr Xaa Xaa Xaa Xaa Xaa Gly
```

```
                  20                  25                  30
Xaa Gly Gly Gly Gly Gly Ile Val Glu Gln Cys Cys Thr Ser Xaa Cys
              35                  40                  45

Ser Leu Xaa Gln Leu Glu Asn Tyr Cys Xaa Xaa
          50                  55

<210> SEQ ID NO 5
<211> LENGTH: 58
<212> TYPE: PRT
<213> ORGANISM: Artificial Sequence
<220> FEATURE:
<223> OTHER INFORMATION: Synthetic Construct

<400> SEQUENCE: 5

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
              20                  25                  30

Ser Gly Gly Gly Gly Gly Ile Val Glu Gln Cys Cys Thr Ser Thr Cys
              35                  40                  45

Ser Leu Asp Gln Leu Glu Asn Tyr Cys Gly
          50                  55

<210> SEQ ID NO 6
<211> LENGTH: 22
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa at position 5 is Gln or Glu
<220> FEATURE:
<221> NAME/KEY: MISC_FEATURE
<222> LOCATION: (10)..(10)
<223> OTHER INFORMATION: Xaa at position 10 is Gln or Glu
<220> FEATURE:
<221> NAME/KEY: MISC_FEATURE
<222> LOCATION: (15)..(15)
<223> OTHER INFORMATION: Xaa at position 15 is Gln or Glu
<220> FEATURE:
<221> NAME/KEY: MISC_FEATURE
<222> LOCATION: (20)..(20)
<223> OTHER INFORMATION: Xaa at position 20 is Gly, Glu, Gln, or is
      absent
<220> FEATURE:
<221> NAME/KEY: MISC_FEATURE
<222> LOCATION: (21)..(21)
<223> OTHER INFORMATION: Xaa at position 21 is Gly or absent
<220> FEATURE:
<221> NAME/KEY: MISC_FEATURE
<222> LOCATION: (22)..(22)
<223> OTHER INFORMATION: Xaa at position 21 is Gly or is absent
<220> FEATURE:
<221> NAME/KEY: MISC_FEATURE
<222> LOCATION: (22)..(22)
<223> OTHER INFORMATION: Xaa at position 22 is Gly or is absent

<400> SEQUENCE: 6

Gly Gly Gly Gly Xaa Gly Gly Gly Gly Xaa Gly Gly Gly Gly Xaa Gly
1               5                   10                  15

Gly Gly Gly Xaa Xaa Xaa
            20

<210> SEQ ID NO 7
<211> LENGTH: 20
<212> TYPE: PRT
```

<213> ORGANISM: Artificial Sequence
<220> FEATURE:
<223> OTHER INFORMATION: Synthetic Construct

<400> SEQUENCE: 7

Gly Gly Gly Gly Gln Gly Gly Gly Gln Gly Gly Gly Gln Gly
1               5                   10                  15

Gly Gly Gly Gly
            20

<210> SEQ ID NO 8
<211> LENGTH: 222
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (16)..(16)
<223> OTHER INFORMATION: Xaa at position 16 is Phe, Gln or Glu
<220> FEATURE:
<221> NAME/KEY: MISC_FEATURE
<222> LOCATION: (18)..(18)
<223> OTHER INFORMATION: Xaa at position 18 is Phe, Gln or Glu
<220> FEATURE:
<221> NAME/KEY: MISC_FEATURE
<222> LOCATION: (37)..(37)
<223> OTHER INFORMATION: Xaa at position 37 is Val or Thr
<220> FEATURE:
<221> NAME/KEY: MISC_FEATURE
<222> LOCATION: (39)..(39)
<223> OTHER INFORMATION: Xaa at position 39 is Val or Thr
<220> FEATURE:
<221> NAME/KEY: MISC_FEATURE
<222> LOCATION: (72)..(72)
<223> OTHER INFORMATION: Xaa at position 72 is Asn, Asp or Gln
<220> FEATURE:
<221> NAME/KEY: MISC_FEATURE
<222> LOCATION: (222)..(222)
<223> OTHER INFORMATION: Xaa at position 222 is Lys or is absent

<400> SEQUENCE: 8

Cys Pro Pro Cys Pro Ala Pro Glu Leu Leu Gly Gly Pro Ser Val Xaa
1               5                   10                  15

Leu Xaa Pro Pro Lys Pro Lys Asp Thr Leu Met Ile Ser Arg Thr Pro
            20                  25                  30

Glu Val Thr Cys Xaa Val Xaa Asp Val Ser His Glu Asp Pro Glu Val
            35                  40                  45

Lys Phe Asn Trp Tyr Val Asp Gly Val Glu Val His Asn Ala Lys Thr
    50                  55                  60

Lys Pro Arg Glu Glu Gln Tyr Xaa Ser Thr Tyr Arg Val Val Ser Val
65                  70                  75                  80

Leu Thr Val Leu His Gln Asp Trp Leu Asn Gly Lys Glu Tyr Lys Cys
            85                  90                  95

Lys Val Ser Asn Lys Ala Leu Pro Ala Pro Ile Glu Lys Thr Ile Ser
        100                 105                 110

Lys Ala Lys Gly Gln Pro Arg Glu Pro Gln Val Tyr Thr Leu Pro Pro
        115                 120                 125

Ser Arg Asp Glu Leu Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
            165                 170                 175

```
Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Xaa
    210                 215                 220
```

<210> SEQ ID NO 9
<211> LENGTH: 223
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (17)..(17)
<223> OTHER INFORMATION: Xaa at position 17 is Phe, Gln or Glu
<220> FEATURE:
<221> NAME/KEY: MISC_FEATURE
<222> LOCATION: (19)..(19)
<223> OTHER INFORMATION: Xaa at position 19 is Phe, Gln or Glu
<220> FEATURE:
<221> NAME/KEY: MISC_FEATURE
<222> LOCATION: (38)..(38)
<223> OTHER INFORMATION: Xaa at position 38 is Val or Thr
<220> FEATURE:
<221> NAME/KEY: MISC_FEATURE
<222> LOCATION: (40)..(40)
<223> OTHER INFORMATION: Xaa at position 40 is Val or Thr
<220> FEATURE:
<221> NAME/KEY: MISC_FEATURE
<222> LOCATION: (73)..(73)
<223> OTHER INFORMATION: Xaa at position 73 is Asn, Asp or Gln
<220> FEATURE:
<221> NAME/KEY: MISC_FEATURE
<222> LOCATION: (185)..(185)
<223> OTHER INFORMATION: Xaa at position 185 is Arg or Lys
<220> FEATURE:
<221> NAME/KEY: MISC_FEATURE
<222> LOCATION: (223)..(223)
<223> OTHER INFORMATION: Xaa at position 223 is Lys or is absent

<400> SEQUENCE: 9

```
Pro Cys Pro Pro Cys Pro Ala Pro Glu Ala Ala Gly Gly Pro Ser Val
1               5                   10                  15

Xaa Leu Xaa Pro Pro Lys Pro Lys Asp Thr Leu Met Ile Ser Arg Thr
            20                  25                  30

Pro Glu Val Thr Cys Xaa Val Xaa Asp Val Ser Gln Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Xaa Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Gln Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175
```

Asp Gly Ser Phe Phe Leu Tyr Ser Xaa Leu Thr Val Asp Lys Ser Arg
            180                 185                 190

Trp Gln Glu Gly Asn Val Phe Ser Cys Ser Val Met His Glu Ala Leu
        195                 200                 205

His Asn His Tyr Thr Gln Lys Ser Leu Ser Leu Gly Xaa
    210                 215                 220

<210> SEQ ID NO 10
<211> LENGTH: 222
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (16)..(16)
<223> OTHER INFORMATION: Xaa at position 16 is Phe, Gln, or Glu
<220> FEATURE:
<221> NAME/KEY: MISC_FEATURE
<222> LOCATION: (18)..(18)
<223> OTHER INFORMATION: Xaa at position 18 is Phe, Gln, or Glu
<220> FEATURE:
<221> NAME/KEY: MISC_FEATURE
<222> LOCATION: (37)..(37)
<223> OTHER INFORMATION: Xaa at position 37 is Val or Thr
<220> FEATURE:
<221> NAME/KEY: MISC_FEATURE
<222> LOCATION: (39)..(39)
<223> OTHER INFORMATION: Xaa at position 39 is Val or Thr
<220> FEATURE:
<221> NAME/KEY: MISC_FEATURE
<222> LOCATION: (72)..(72)
<223> OTHER INFORMATION: Xaa at position 72 is Asn, Asp, or Gln
<220> FEATURE:
<221> NAME/KEY: MISC_FEATURE
<222> LOCATION: (222)..(222)
<223> OTHER INFORMATION: Xaa at position 222 is Lys or is absent

<400> SEQUENCE: 10

Glu Cys Pro Pro Cys Pro Ala Pro Pro Val Ala Gly Pro Ser Val Xaa
1               5                   10                  15

Leu Xaa Pro Pro Lys Pro Lys Asp Thr Leu Met Ile Ser Arg Thr Pro
            20                  25                  30

Glu Val Thr Cys Xaa Val Xaa Asp Val Ser His Glu Asp Pro Glu Val
        35                  40                  45

Gln Phe Asn Trp Tyr Val Asp Gly Val Glu Val His Asn Ala Lys Thr
    50                  55                  60

Lys Pro Arg Glu Glu Gln Phe Xaa Ser Thr Phe Arg Val Val Ser Val
65                  70                  75                  80

Leu Thr Val Val His Gln Asp Trp Leu Asn Gly Lys Glu Tyr Lys Cys
            85                  90                  95

Lys Val Ser Asn Lys Gly Leu Pro Ala Pro Ile Glu Lys Thr Ile Ser
            100                 105                 110

Lys Thr Lys Gly Gln Pro Arg Glu Pro Gln Val Tyr Thr Leu Pro Pro
            115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Met Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Xaa
        210                 215                 220

<210> SEQ ID NO 11
<211> LENGTH: 303
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa at position 1 is Phe, Gln, or Ala
<220> FEATURE:
<221> NAME/KEY: MISC_FEATURE
<222> LOCATION: (2)..(2)
<223> OTHER INFORMATION: Xaa at position 2 is Val or Gly
<220> FEATURE:
<221> NAME/KEY: MISC_FEATURE
<222> LOCATION: (3)..(3)
<223> OTHER INFORMATION: Xaa at position 3 is Asn, Lys, Asp, Gly, Gln,
      Ala, or Glu
<220> FEATURE:
<221> NAME/KEY: MISC_FEATURE
<222> LOCATION: (16)..(16)
<223> OTHER INFORMATION: Xaa at position 16 is Glu, Tyr, Gln, or His
<220> FEATURE:
<221> NAME/KEY: MISC_FEATURE
<222> LOCATION: (25)..(25)
<223> OTHER INFORMATION: Xaa at position 25 is His or Phe
<220> FEATURE:
<221> NAME/KEY: MISC_FEATURE
<222> LOCATION: (27)..(27)
<223> OTHER INFORMATION: Xaa at position 27 is Gly, Thr, Ser, His, Val,
      or is absent
<220> FEATURE:
<221> NAME/KEY: MISC_FEATURE
<222> LOCATION: (28)..(28)
<223> OTHER INFORMATION: Xaa at position 28 is Gly, Glu, Pro, Lys, Asp,
      Ser, His, or is absent
<220> FEATURE:
<221> NAME/KEY: MISC_FEATURE
<222> LOCATION: (29)..(29)
<223> OTHER INFORMATION: Xaa at position 29 is Gly, Glu, Lys, Pro, Gln,
      Asp, His, or is absent
<220> FEATURE:
<221> NAME/KEY: MISC_FEATURE
<222> LOCATION: (30)..(30)
<223> OTHER INFORMATION: Xaa at position 30 is Gly, Thr, Ser, Glu, Lys,
      Ala, or is absent
<220> FEATURE:
<221> NAME/KEY: MISC_FEATURE
<222> LOCATION: (31)..(31)
<223> OTHER INFORMATION: Xaa at position 31 is Gly, or is absent
<220> FEATURE:
<221> NAME/KEY: MISC_FEATURE
<222> LOCATION: (33)..(33)
<223> OTHER INFORMATION: Xaa at position 33 is Gly, Ser, or is absent
<220> FEATURE:
<221> NAME/KEY: MISC_FEATURE
<222> LOCATION: (47)..(47)
<223> OTHER INFORMATION: Xaa at position 47 is Thr or Ile
<220> FEATURE:
<221> NAME/KEY: MISC_FEATURE
<222> LOCATION: (51)..(51)
<223> OTHER INFORMATION: Xaa at position 51 is Asp, Tyr, Gln, or Glu
<220> FEATURE:
<221> NAME/KEY: MISC_FEATURE
<222> LOCATION: (58)..(58)
<223> OTHER INFORMATION: Xaa at position 58 is Gly, Asn, Ser or Ala
<220> FEATURE:
<221> NAME/KEY: MISC_FEATURE
<222> LOCATION: (59)..(59)
<223> OTHER INFORMATION: Xaa at position 59 is any naturally occurring

```
              amino acid, or is absent
<220> FEATURE:
<221> NAME/KEY: MISC_FEATURE
<222> LOCATION: (64)..(64)
<223> OTHER INFORMATION: Xaa at position 64 is Gln or Glu
<220> FEATURE:
<221> NAME/KEY: MISC_FEATURE
<222> LOCATION: (69)..(69)
<223> OTHER INFORMATION: Xaa at position 69 is Gln or Glu
<220> FEATURE:
<221> NAME/KEY: MISC_FEATURE
<222> LOCATION: (74)..(74)
<223> OTHER INFORMATION: Xaa at position 74 is Gln or Glu
<220> FEATURE:
<221> NAME/KEY: MISC_FEATURE
<222> LOCATION: (79)..(79)
<223> OTHER INFORMATION: Xaa at position 79 is Gly, Glu, Gln, or is
      absent
<220> FEATURE:
<221> NAME/KEY: MISC_FEATURE
<222> LOCATION: (80)..(80)
<223> OTHER INFORMATION: Xaa at position 80 is Gly or is absent
<220> FEATURE:
<221> NAME/KEY: MISC_FEATURE
<222> LOCATION: (81)..(81)
<223> OTHER INFORMATION: Xaa at position 81 is Gly or is absent
<220> FEATURE:
<221> NAME/KEY: MISC_FEATURE
<222> LOCATION: (82)..(82)
<223> OTHER INFORMATION: Xaa at position 82 is Glu or Pro
<220> FEATURE:
<221> NAME/KEY: MISC_FEATURE
<222> LOCATION: (90)..(90)
<223> OTHER INFORMATION: Xaa at position 90 is Glu or Pro
<220> FEATURE:
<221> NAME/KEY: MISC_FEATURE
<222> LOCATION: (91)..(91)
<223> OTHER INFORMATION: Xaa at position 91 is Ala and Val
<220> FEATURE:
<221> NAME/KEY: MISC_FEATURE
<222> LOCATION: (94)..(94)
<223> OTHER INFORMATION: Xaa at position 94 is Gly or is absent
<220> FEATURE:
<221> NAME/KEY: MISC_FEATURE
<222> LOCATION: (125)..(125)
<223> OTHER INFORMATION: Xaa at position 125 is Gln or His
<220> FEATURE:
<221> NAME/KEY: MISC_FEATURE
<222> LOCATION: (157)..(157)
<223> OTHER INFORMATION: Xaa at position 157 is Tyr or Phe
<220> FEATURE:
<221> NAME/KEY: MISC_FEATURE
<222> LOCATION: (166)..(166)
<223> OTHER INFORMATION: Xaa at position 166 is Leu or Val
<220> FEATURE:
<221> NAME/KEY: MISC_FEATURE
<222> LOCATION: (187)..(187)
<223> OTHER INFORMATION: Xaa at position 187 is Ser or Ala
<220> FEATURE:
<221> NAME/KEY: MISC_FEATURE
<222> LOCATION: (188)..(188)
<223> OTHER INFORMATION: Xaa at position 188 is Ser or Pro
<220> FEATURE:
<221> NAME/KEY: MISC_FEATURE
<222> LOCATION: (196)..(196)
<223> OTHER INFORMATION: Xaa at position 196 is Ala or Thr
<220> FEATURE:
<221> NAME/KEY: MISC_FEATURE
<222> LOCATION: (212)..(212)
<223> OTHER INFORMATION: Xaa at position 212 is Gln or Arg
<220> FEATURE:
<221> NAME/KEY: MISC_FEATURE
<222> LOCATION: (254)..(254)
<223> OTHER INFORMATION: Xaa at position 254 is Val or Met
<220> FEATURE:
<221> NAME/KEY: MISC_FEATURE
<222> LOCATION: (266)..(266)
<223> OTHER INFORMATION: Xaa at position 266 is Arg or Lys
<220> FEATURE:
```

<221> NAME/KEY: MISC_FEATURE
<222> LOCATION: (276)..(276)
<223> OTHER INFORMATION: Xaa at position 276 is Glu or Gln
<220> FEATURE:
<221> NAME/KEY: MISC_FEATURE
<222> LOCATION: (302)..(302)
<223> OTHER INFORMATION: Xaa at position 302 is Leu or Pro

<400> SEQUENCE: 11

Xaa Xaa Xaa Gln His Leu Cys Gly Ser His Leu Val Glu Ala Leu Xaa
1               5                   10                  15

Leu Val Cys Gly Glu Arg Gly Phe Xaa Tyr Xaa Xaa Xaa Xaa Xaa Gly
            20                  25                  30

Xaa Gly Gly Gly Gly Ile Val Glu Gln Cys Cys Thr Ser Xaa Cys
        35                  40                  45

Ser Leu Xaa Gln Leu Glu Asn Tyr Cys Xaa Xaa Gly Gly Gly Xaa
    50                  55                  60

Gly Gly Gly Gly Xaa Gly Gly Gly Xaa Gly Gly Gly Xaa Xaa
65              70                  75                  80

Xaa Xaa Cys Pro Pro Cys Pro Ala Pro Xaa Xaa Ala Gly Xaa Pro Ser
                85                  90                  95

Val Phe Leu Phe Pro Pro Lys Pro Lys Asp Thr Leu Met Ile Ser Arg
            100                 105                 110

Thr Pro Glu Val Thr Cys Val Val Val Asp Val Ser Xaa Glu Asp Pro
            115                 120                 125

Glu Val Gln Phe Asn Trp Tyr Val Asp Gly Val Glu Val His Asn Ala
            130                 135                 140

Lys Thr Lys Pro Arg Glu Glu Gln Phe Asn Ser Thr Xaa Arg Val Val
145                 150                 155                 160

Ser Val Leu Thr Val Xaa His Gln Asp Trp Leu Asn Gly Lys Glu Tyr
                165                 170                 175

Lys Cys Lys Val Ser Asn Lys Gly Leu Pro Xaa Xaa Ile Glu Lys Thr
            180                 185                 190

Ile Ser Lys Xaa Lys Gly Gln Pro Arg Glu Pro Gln Val Tyr Thr Leu
            195                 200                 205

Pro Pro Ser Xaa Glu Glu Met Thr Lys Asn Gln Val Ser Leu Thr Cys
        210                 215                 220

Leu Val Lys Gly Phe Tyr Pro Ser Asp Ile Ala Val Glu Trp Glu Ser
225                 230                 235                 240

Asn Gly Gln Pro Glu Asn Asn Tyr Lys Thr Thr Pro Xaa Leu Asp
            245                 250                 255

Ser Asp Gly Ser Phe Phe Leu Tyr Ser Xaa Leu Thr Val Asp Lys Ser
            260                 265                 270

Arg Trp Gln Xaa Gly Asn Val Phe Ser Cys Ser Val Met His Glu Ala
            275                 280                 285

Leu His Asn His Tyr Thr Gln Lys Ser Leu Ser Leu Ser Xaa Gly
    290                 295                 300

<210> SEQ ID NO 12
<211> LENGTH: 299
<212> TYPE: PRT
<213> ORGANISM: Artificial Sequence
<220> FEATURE:
<223> OTHER INFORMATION: Synthetic Construct

<400> SEQUENCE: 12

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly
            20                  25                  30

Ser Gly Gly Gly Gly Ile Val Glu Gln Cys Cys Thr Ser Thr Cys
            35                  40                  45

Ser Leu Asp Gln Leu Glu Asn Tyr Cys Gly Gly Gly Gly Gln Gly
    50                  55                  60

Gly Gly Gln Gly Gly Gly Gln Gly Gly Gly Gly Glu Cys
65                  70                  75                  80

Pro Pro Cys Pro Ala Pro Val Ala Gly Pro Ser Val Phe Leu Phe
                85                  90                  95

Pro Pro Lys Pro Lys Asp Thr Leu Met Ile Ser Arg Thr Pro Glu Val
                100                 105                 110

Thr Cys Val Val Val Asp Val Ser His Glu Asp Pro Glu Val Gln Phe
                115                 120                 125

Asn Trp Tyr Val Asp Gly Val Glu Val His Asn Ala Lys Thr Lys Pro
    130                 135                 140

Arg Glu Glu Gln Phe Asn Ser Thr Phe Arg Val Val Ser Val Leu Thr
145                 150                 155                 160

Val Val His Gln Asp Trp Leu Asn Gly Lys Glu Tyr Lys Cys Lys Val
                165                 170                 175

Ser Asn Lys Gly Leu Pro Ala Pro Ile Glu Lys Thr Ile Ser Lys Thr
                180                 185                 190

Lys Gly Gln Pro Arg Glu Pro Gln Val Tyr Thr Leu Pro Pro Ser Arg
            195                 200                 205

Glu Glu Met Thr Lys Asn Gln Val Ser Leu Thr Cys Leu Val Lys Gly
            210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Met Leu Asp Ser Asp Gly Ser
                245                 250                 255

Phe Phe Leu Tyr Ser Lys Leu Thr Val Asp Lys Ser Arg Trp Gln Gln
                260                 265                 270

Gly Asn Val Phe Ser Cys Ser Val Met His Glu Ala Leu His Asn His
            275                 280                 285

Tyr Thr Gln Lys Ser Leu Ser Leu Ser Pro Gly
    290                 295

<210> SEQ ID NO 13
<211> LENGTH: 21
<212> TYPE: PRT
<213> ORGANISM: Homo sapiens

<400> SEQUENCE: 13

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 14
<211> LENGTH: 30
<212> TYPE: PRT
<213> ORGANISM: Homo sapiens

<400> SEQUENCE: 14

Phe Val Asn Gln His Leu Cys Gly Ser His Leu Val Glu Ala Leu Tyr
1               5                   10                  15

```
Leu Val Cys Gly Glu Arg Gly Phe Phe Tyr Thr Pro Lys Thr
            20                  25                  30
```

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

```
Gly Gly Ser Gly Gly Gly Gly
1               5
```

<210> SEQ ID NO 16
<211> LENGTH: 300
<212> TYPE: PRT
<213> ORGANISM: Artificial Sequence
<220> FEATURE:
<223> OTHER INFORMATION: Synthetic Construct

<400> SEQUENCE: 16

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Glu Thr Gly Gly
            20                  25                  30

Gly Gly Gly Gly Gly Ile Val Glu Gln Cys Cys Thr Ser Ile Cys Ser
        35                  40                  45

Leu Tyr Gln Leu Glu Asn Tyr Cys Gly Gly Gly Gly Ser Gly Gly
    50                  55                  60

Gly Gly Ser Gly Gly Gly Gly Ser Glu Ser Lys Tyr Gly Pro Pro Cys
65                  70                  75                  80

Pro Pro Cys Pro Ala Pro Glu Ala Ala Gly Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Ser Gln Glu Asp Pro Glu Val Gln
        115                 120                 125

Phe Asn Trp Tyr Val Asp Gly Val Glu Val His Asn Ala Lys Thr Lys
    130                 135                 140

Pro Arg Glu Glu Gln Phe Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Gly Leu Pro Ser Ser Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Gln Glu Glu Met Thr Lys Asn Gln Val Ser Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Arg Leu Thr Val Asp Lys Ser Arg Trp Gln
            260                 265                 270

Glu Gly Asn Val Phe Ser Cys Ser Val Met His Glu Ala Leu His Asn
```

His Tyr Thr Gln Lys Ser Leu Ser Leu Ser Leu Gly
            290                 295                 300

<210> SEQ ID NO 17
<211> LENGTH: 302
<212> TYPE: PRT
<213> ORGANISM: Artificial Sequence
<220> FEATURE:
<223> OTHER INFORMATION: Synthetic Construct

<400> SEQUENCE: 17

Phe Val Asn Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Ile Cys
        35                  40                  45

Ser Leu Asp Gln Leu Glu Asn Tyr Cys Gly Gly Gly Gly Gln Gly
    50                  55                  60

Gly Gly Gln Gly Gly Gly Gln Gly Gly Gly Gln Gly
65                  70                  75                  80

Pro Cys Pro Pro Cys Pro Ala Pro Glu Ala Ala Gly Gly Pro Ser Val
                85                  90                  95

Phe Leu Phe Pro Pro Lys Pro Lys Asp Thr Leu Met Ile Ser Arg Thr
            100                 105                 110

Pro Glu Val Thr Cys Val Val Val Asp Val Ser Gln Glu Asp Pro Glu
        115                 120                 125

Val Gln Phe Asn Trp Tyr Val Asp Gly Val Glu Val His Asn Ala Lys
    130                 135                 140

Thr Lys Pro Arg Glu Glu Gln Phe Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Gly Leu Pro Ser Ser Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Gln Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Arg Leu Thr Val Asp Lys Ser Arg
            260                 265                 270

Trp Gln Glu Gly Asn Val Phe Ser Cys Ser Val Met His Glu Ala Leu
        275                 280                 285

His Asn His Tyr Thr Gln Lys Ser Leu Ser Leu Ser Leu Gly
    290                 295                 300

<210> SEQ ID NO 18
<211> LENGTH: 297
<212> TYPE: PRT
<213> ORGANISM: Artificial Sequence
<220> FEATURE:
<223> OTHER INFORMATION: Synthetic Construct

<400> SEQUENCE: 18

```
Phe Val Asn Gln His Leu Cys Gly Ser His Leu Val Glu Ala Leu Glu
1               5                   10                  15
Leu Val Cys Gly Glu Arg Gly Phe His Tyr Gly Gly Gly Gly Gly Ser
            20                  25                  30
Gly Gly Gly Gly Gly Ile Val Glu Gln Cys Cys Thr Ser Ile Cys Ser
        35                  40                  45
Leu Asp Gln Leu Glu Asn Tyr Cys Gly Gly Gly Glu Gly Gly Gly
    50                  55                  60
Gly Gly Glu Gly Gly Gly Glu Gly Gly Gly Glu Cys Pro Pro
65                  70                  75                  80
Cys Pro Ala Pro Pro Val Ala Gly Pro Ser Val Phe Leu Phe Pro Pro
                85                  90                  95
Lys Pro Lys Asp Thr Leu Met Ile Ser Arg Thr Pro Glu Val Thr Cys
            100                 105                 110
Val Val Val Asp Val Ser His Glu Asp Pro Glu Val Gln Phe Asn Trp
        115                 120                 125
Tyr Val Asp Gly Val Glu Val His Asn Ala Lys Thr Lys Pro Arg Glu
    130                 135                 140
Glu Gln Phe Asn Ser Thr Phe Arg Val Val Ser Val Leu Thr Val Val
145                 150                 155                 160
His Gln Asp Trp Leu Asn Gly Lys Glu Tyr Lys Cys Lys Val Ser Asn
                165                 170                 175
Lys Gly Leu Pro Ala Pro Ile Glu Lys Thr Ile Ser Lys Thr Lys Gly
            180                 185                 190
Gln Pro Arg Glu Pro Gln Val Tyr Thr Leu Pro Pro Ser Arg Glu Glu
        195                 200                 205
Met Thr Lys Asn Gln Val Ser Leu Thr Cys Leu Val Lys Gly Phe Tyr
    210                 215                 220
Pro Ser Asp Ile Ala Val Glu Trp Glu Ser Asn Gly Gln Pro Glu Asn
225                 230                 235                 240
Asn Tyr Lys Thr Thr Pro Pro Met Leu Asp Ser Asp Gly Ser Phe Phe
                245                 250                 255
Leu Tyr Ser Lys Leu Thr Val Asp Lys Ser Arg Trp Gln Gln Gly Asn
            260                 265                 270
Val Phe Ser Cys Ser Val Met His Glu Ala Leu His Asn His Tyr Thr
        275                 280                 285
Gln Lys Ser Leu Ser Leu Ser Pro Gly
    290                 295
```

<210> SEQ ID NO 19
<211> LENGTH: 302
<212> TYPE: PRT
<213> ORGANISM: Artificial Sequence
<220> FEATURE:
<223> OTHER INFORMATION: Synthetic Construct

<400> SEQUENCE: 19

```
Phe Val Asn Gln His Leu Cys Gly Ser His Leu Val Glu Ala Leu Glu
1               5                   10                  15
Leu Val Cys Gly Glu Arg Gly Phe His Tyr Gly Gly Gly Gly Gly
            20                  25                  30
Ser Gly Gly Gly Gly Ile Val Glu Gln Cys Cys Thr Ser Thr Cys
        35                  40                  45
```

```
Ser Leu Asp Gln Leu Glu Asn Tyr Cys Gly Gly Gly Gly Gln Gly
    50                  55                  60

Gly Gly Gly Gln Gly Gly Gly Gln Gly Gly Gly Gln Gly Gly
65                  70                  75                  80

Pro Cys Pro Pro Cys Pro Ala Pro Glu Ala Ala Gly Gly Pro Ser Val
                85                  90                  95

Phe Leu Phe Pro Pro Lys Pro Lys Asp Thr Leu Met Ile Ser Arg Thr
                100                 105                 110

Pro Glu Val Thr Cys Val Val Val Asp Val Ser Gln Glu Asp Pro Glu
                115                 120                 125

Val Gln Phe Asn Trp Tyr Val Asp Gly Val Glu Val His Asn Ala Lys
130                 135                 140

Thr Lys Pro Arg Glu Glu Gln Phe Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Gly Leu Pro Ser Ser Ile Glu Lys Thr Ile
                180                 185                 190

Ser Lys Ala Lys Gly Gln Pro Arg Glu Pro Gln Val Tyr Thr Leu Pro
                195                 200                 205

Pro Ser Gln Glu Glu Met Thr Lys Asn Gln Val Ser Leu Thr Cys Leu
210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Arg Leu Thr Val Asp Lys Ser Arg
                260                 265                 270

Trp Gln Glu Gly Asn Val Phe Ser Cys Ser Val Met His Glu Ala Leu
                275                 280                 285

His Asn His Tyr Thr Gln Lys Ser Leu Ser Leu Ser Leu Gly
                290                 295                 300
```

<210> SEQ ID NO 20
<211> LENGTH: 302
<212> TYPE: PRT
<213> ORGANISM: Artificial Sequence
<220> FEATURE:
<223> OTHER INFORMATION: Synthetic Construct

<400> SEQUENCE: 20

```
Phe Val Gly Gln His Leu Cys Gly Ser His Leu Val Glu Ala Leu Glu
1               5                   10                  15

Leu Val Cys Gly Glu Arg Gly Phe His Tyr Gly Gly Gly Gly Gly
                20                  25                  30

Ser Gly Gly Gly Gly Ile Val Glu Gln Cys Cys Thr Ser Ile Cys
                35                  40                  45

Ser Leu Asp Gln Leu Glu Asn Tyr Cys Gly Gly Gly Gly Gln Gly
    50                  55                  60

Gly Gly Gly Gln Gly Gly Gly Gln Gly Gly Gly Gln Gly Gly
65                  70                  75                  80

Pro Cys Pro Pro Cys Pro Ala Pro Glu Ala Ala Gly Gly Pro Ser Val
                85                  90                  95

Phe Leu Phe Pro Pro Lys Pro Lys Asp Thr Leu Met Ile Ser Arg Thr
                100                 105                 110
```

```
Pro Glu Val Thr Cys Val Val Asp Val Ser Gln Glu Asp Pro Glu
            115                 120                 125

Val Gln Phe Asn Trp Tyr Val Asp Gly Val Glu Val His Asn Ala Lys
    130                 135                 140

Thr Lys Pro Arg Glu Glu Gln Phe Asn Ser Thr Tyr Arg Val Val Ser
145                 150                 155                 160

Val Leu Thr Val Leu His Gln Asp Trp Leu Asn Gly Lys Glu Tyr Lys
                165                 170                 175

Cys Lys Val Ser Asn Lys Gly Leu Pro Ser Ser Ile Glu Lys Thr Ile
            180                 185                 190

Ser Lys Ala Lys Gly Gln Pro Arg Glu Pro Gln Val Tyr Thr Leu Pro
        195                 200                 205

Pro Ser Gln Glu Glu Met Thr Lys Asn Gln Val Ser Leu Thr Cys Leu
    210                 215                 220

Val Lys Gly Phe Tyr Pro Ser Asp Ile Ala Val Glu Trp Glu Ser Asn
225                 230                 235                 240

Gly Gln Pro Glu Asn Asn Tyr Lys Thr Thr Pro Pro Val Leu Asp Ser
                245                 250                 255

Asp Gly Ser Phe Phe Leu Tyr Ser Arg Leu Thr Val Asp Lys Ser Arg
            260                 265                 270

Trp Gln Glu Gly Asn Val Phe Ser Cys Ser Val Met His Glu Ala Leu
        275                 280                 285

His Asn His Tyr Thr Gln Lys Ser Leu Ser Leu Ser Leu Gly
    290                 295                 300

<210> SEQ ID NO 21
<211> LENGTH: 297
<212> TYPE: PRT
<213> ORGANISM: Artificial Sequence
<220> FEATURE:
<223> OTHER INFORMATION: Synthetic Construct

<400> SEQUENCE: 21

Ala Gly Gly Gln His Leu Cys Gly Ser His Leu Val Glu Ala Leu Glu
1               5                   10                  15

Leu Val Cys Gly Glu Arg Gly Phe His Tyr Gly Gly Gly Gly Gly Ser
            20                  25                  30

Gly Gly Gly Gly Gly Ile Val Glu Gln Cys Cys Thr Ser Ile Cys Ser
        35                  40                  45

Leu Asp Gln Leu Glu Asn Tyr Cys Gly Gly Gly Gly Gln Gly Gly
    50                  55                  60

Gly Gly Gln Gly Gly Gly Gly Gln Gly Gly Gly Gly Glu Cys Pro Pro
65                  70                  75                  80

Cys Pro Ala Pro Pro Val Ala Gly Pro Ser Val Phe Leu Phe Pro Pro
                85                  90                  95

Lys Pro Lys Asp Thr Leu Met Ile Ser Arg Thr Pro Glu Val Thr Cys
            100                 105                 110

Val Val Val Asp Val Ser His Glu Asp Pro Glu Val Gln Phe Asn Trp
        115                 120                 125

Tyr Val Asp Gly Val Glu Val His Asn Ala Lys Thr Lys Pro Arg Glu
    130                 135                 140

Glu Gln Phe Asn Ser Thr Phe Arg Val Val Ser Val Leu Thr Val Val
145                 150                 155                 160

His Gln Asp Trp Leu Asn Gly Lys Glu Tyr Lys Cys Lys Val Ser Asn
                165                 170                 175
```

-continued

Lys Gly Leu Pro Ala Pro Ile Glu Lys Thr Ile Ser Lys Thr Lys Gly
            180                 185                 190

Gln Pro Arg Glu Pro Gln Val Tyr Thr Leu Pro Pro Ser Arg Glu Glu
        195                 200                 205

Met Thr Lys Asn Gln Val Ser Leu Thr Cys Leu Val Lys Gly Phe Tyr
    210                 215                 220

Pro Ser Asp Ile Ala Val Glu Trp Glu Ser Asn Gly Gln Pro Glu Asn
225                 230                 235                 240

Asn Tyr Lys Thr Thr Pro Pro Met Leu Asp Ser Asp Gly Ser Phe Phe
                245                 250                 255

Leu Tyr Ser Lys Leu Thr Val Asp Lys Ser Arg Trp Gln Gln Gly Asn
            260                 265                 270

Val Phe Ser Cys Ser Val Met His Glu Ala Leu His Asn His Tyr Thr
        275                 280                 285

Gln Lys Ser Leu Ser Leu Ser Pro Gly
    290                 295

<210> SEQ ID NO 22
<211> LENGTH: 299
<212> TYPE: PRT
<213> ORGANISM: Artificial Sequence
<220> FEATURE:
<223> OTHER INFORMATION: Synthetic Construct

<400> SEQUENCE: 22

Phe Val Asn Gln His Leu Cys Gly Ser His Leu Val Glu Ala Leu Glu
1               5                   10                  15

Leu Val Cys Gly Glu Arg Gly Phe His Tyr Thr Pro Lys Thr Gly Gly
            20                  25                  30

Ser Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gln Gly
    50                  55                  60

Gly Gly Gly Gln Gly Gly Gly Gln Gly Gly Gly Gly Glu Cys
65                  70                  75                  80

Pro Pro Cys Pro Ala Pro Pro Val Ala Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Gln Phe
        115                 120                 125

Asn Trp Tyr Val Asp Gly Val Glu Val His Asn Ala Lys Thr Lys Pro
    130                 135                 140

Arg Glu Glu Gln Phe Asn Ser Thr Phe Arg Val Val Ser Val Leu Thr
145                 150                 155                 160

Val Val His Gln Asp Trp Leu Asn Gly Lys Glu Tyr Lys Cys Lys Val
                165                 170                 175

Ser Asn Lys Gly Leu Pro Ala Pro Ile Glu Lys Thr Ile Ser Lys Thr
            180                 185                 190

Lys Gly Gln Pro Arg Glu Pro Gln Val Tyr Thr Leu Pro Pro Ser Arg
        195                 200                 205

Glu Glu Met Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
225                 230                 235                 240

```
Glu Asn Asn Tyr Lys Thr Thr Pro Pro Met Leu Asp Ser Asp Gly Ser
            245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
            275                 280                 285

Tyr Thr Gln Lys Ser Leu Ser Leu Ser Pro Gly
            290                 295

<210> SEQ ID NO 23
<211> LENGTH: 298
<212> TYPE: PRT
<213> ORGANISM: Artificial Sequence
<220> FEATURE:
<223> OTHER INFORMATION: Synthetic Construct

<400> SEQUENCE: 23

Phe Val Asn Gln His Leu Cys Gly Ser His Leu Val Glu Ala Leu Glu
1               5                   10                  15

Leu Val Cys Gly Glu Arg Gly Phe Phe Tyr Thr Glu Thr Gly Gly
            20                  25                  30

Gly Gly Gly Gly Gly Ile Val Glu Gln Cys Cys Thr Ser Ile Cys Ser
            35                  40                  45

Leu Tyr Gln Leu Glu Asn Tyr Cys Gly Gly Gly Gly Ser Gly Gly
50                  55                  60

Gly Gly Ser Gly Gly Gly Ser Gly Gly Gly Ser Glu Cys Pro
65                  70                  75                  80

Pro Cys Pro Ala Pro Pro Val Ala Gly Pro Ser Val Phe Leu Phe Pro
            85                  90                  95

Pro Lys Pro Lys Asp Thr Leu Met Ile Ser Arg Thr Pro Glu Val Thr
            100                 105                 110

Cys Val Val Val Asp Val Ser His Glu Asp Pro Glu Val Gln Phe Asn
            115                 120                 125

Trp Tyr Val Asp Gly Val Glu Val His Asn Ala Lys Thr Lys Pro Arg
            130                 135                 140

Glu Glu Gln Phe Asn Ser Thr Phe Arg Val Val Ser Val Leu Thr Val
145                 150                 155                 160

Val His Gln Asp Trp Leu Asn Gly Lys Glu Tyr Lys Cys Lys Val Ser
            165                 170                 175

Asn Lys Gly Leu Pro Ala Pro Ile Glu Lys Thr Ile Ser Lys Thr Lys
            180                 185                 190

Gly Gln Pro Arg Glu Pro Gln Val Tyr Thr Leu Pro Pro Ser Arg Glu
            195                 200                 205

Glu Met Thr Lys Asn Gln Val Ser Leu Thr Cys Leu Val Lys Gly Phe
            210                 215                 220

Tyr Pro Ser Asp Ile Ala Val Glu Trp Glu Ser Asn Gly Gln Pro Glu
225                 230                 235                 240

Asn Asn Tyr Lys Thr Thr Pro Pro Met Leu Asp Ser Asp Gly Ser Phe
            245                 250                 255

Phe Leu Tyr Ser Lys Leu Thr Val Asp Lys Ser Arg Trp Gln Gln Gly
            260                 265                 270

Asn Val Phe Ser Cys Ser Val Met His Glu Ala Leu His Asn His Tyr
            275                 280                 285

Thr Gln Lys Ser Leu Ser Leu Ser Pro Gly
            290                 295
```

-continued

<210> SEQ ID NO 24
<211> LENGTH: 299
<212> TYPE: PRT
<213> ORGANISM: Artificial Sequence
<220> FEATURE:
<223> OTHER INFORMATION: Synthetic Construct

<400> SEQUENCE: 24

```
Phe Val Gly Gln His Leu Cys Gly Ser His Leu Val Glu Ala Leu Glu
1               5                   10                  15

Leu Val Cys Gly Glu Arg Gly Phe His Tyr Gly Gly Gly Gly Gly Gly
            20                  25                  30

Ser Gly Gly Gly Gly Gly Ile Val Glu Gln Cys Cys Thr Ser Thr Cys
        35                  40                  45

Ser Leu Asp Gln Leu Glu Asn Tyr Cys Gly Gly Gly Gly Gln Gly
    50                  55                  60

Gly Gly Gln Gly Gly Gly Gln Gly Gly Gly Gly Glu Cys
65                  70                  75                  80

Pro Pro Cys Pro Ala Pro Pro Val Ala Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Gln Phe
        115                 120                 125

Asn Trp Tyr Val Asp Gly Val Glu Val His Asn Ala Lys Thr Lys Pro
    130                 135                 140

Arg Glu Glu Gln Phe Asn Ser Thr Phe Arg Val Val Ser Val Leu Thr
145                 150                 155                 160

Val Val His Gln Asp Trp Leu Asn Gly Lys Glu Tyr Lys Cys Lys Val
                165                 170                 175

Ser Asn Lys Gly Leu Pro Ala Pro Ile Glu Lys Thr Ile Ser Lys Thr
            180                 185                 190

Lys Gly Gln Pro Arg Glu Pro Gln Val Tyr Thr Leu Pro Pro Ser Arg
        195                 200                 205

Glu Glu Met Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
225                 230                 235                 240

Glu Asn Asn Tyr Lys Thr Thr Pro Pro Met Leu Asp Ser Asp Gly Ser
                245                 250                 255

Phe Phe Leu Tyr Ser Lys Leu Thr Val Asp Lys Ser Arg Trp Gln Gln
            260                 265                 270

Gly Asn Val Phe Ser Cys Ser Val Met His Glu Ala Leu His Asn His
        275                 280                 285

Tyr Thr Gln Lys Ser Leu Ser Leu Ser Pro Gly
    290                 295
```

<210> SEQ ID NO 25
<211> LENGTH: 31
<212> TYPE: PRT
<213> ORGANISM: Homo sapiens

<400> SEQUENCE: 25

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
```

```
                        20                  25                  30

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa at position 5 is Gln, Glu or Ser

<400> SEQUENCE: 26

Gly Gly Gly Gly Xaa
1               5
```

FUSION PROTEINS

The present invention relates to fusion proteins for use in the treatment of diabetes. More particularly, the invention relates to fusion proteins comprising an insulin receptor agonist fused to a human IgG Fc region with a peptide linker, and the use of such proteins in the treatment of diabetes. The fusion proteins of the present invention have an extended time action profile and are useful for providing protracted basal glucose control and suppression of hepatic glucose output.

Diabetes mellitus is a chronic disorder characterized by hyperglycemia resulting from defects in insulin secretion, insulin action, or both. Type 1 diabetes mellitus is characterized by little or no insulin secretory capacity, and patients with type 1 diabetes mellitus require insulin for survival. Type 2 diabetes mellitus is characterized by elevated blood glucose levels resulting from impaired insulin secretion, insulin resistance, excessive hepatic glucose output, and/or contributions from all of the above. In at least one-third of patients with Type 2 diabetes mellitus, the disease progresses to an absolute requirement for insulin therapy.

In order to achieve normal glycemia, insulin replacement therapy is desired to parallel, as closely as possible, the pattern of endogenous insulin secretion in normal individuals. The daily physiological demand for insulin fluctuates and can be separated into two phases: (a) the mealtime phase requiring a pulse (bolus) of insulin to dispose of the meal-related blood glucose surge, and (b) the inter-meal phase requiring a sustained (basal) amount of insulin to regulate hepatic glucose output for maintaining optimal fasting blood glucose.

Because Type 1 diabetes patients produce little or no insulin, effective insulin therapy for Type 1 diabetics generally involves the use of two types of exogenously administered insulin: a rapid-acting, mealtime insulin provided by bolus injections, and a long-acting, basal insulin, administered once or twice daily to control blood glucose levels between meals. Treatment of patients with Type 2 diabetes typically begins with prescribed weight loss, exercise, and a diabetic diet, but when these measures fail to control elevated blood sugars, then oral medications and incretin-based therapy, such as administration of glucagon-like peptide-1 (GLP-1) receptor agonists and/or dipeptidyl peptidase 4 (DPP-4) inhibitors that enable increased incretin levels, may be necessary. When these medications are still insufficient, treatment with insulin is considered. Type 2 diabetes patients whose disease has progressed to the point that insulin therapy is required are generally started on a single daily injection of a long-acting, basal insulin, although mealtime injections of rapid-acting insulins may be included, as necessary, in some cases.

Several types of basal insulins are currently available. Insulin glargine, sold under the tradename LANTUS®, comprises a modified insulin structure in which the asparagine at position 21 in the insulin A-chain is replaced with glycine, and two arginines are added to the C-terminus of the B-chain. Insulin detemir, sold under the tradename LEVEMIR®, comprises a modified insulin structure in which the threonine at position 30 of the B-chain has been deleted and the lysine at position 29 of the B-chain has been derivatized through the covalent linkage of a 14-carbon, myristoyl fatty acid to the E-amine group of lysine at B29. Insulin degludec, available in Europe and Japan under the tradename TRESIBA®, comprises a modified insulin structure in which the threonine at position 30 of the B-chain has been deleted, and the ε-amino group of the lysine at position 29 of the B-chain is covalently derivatized with hexadecandioic acid via a γ-L-glutamic acid linker. All of these insulins are indicated for once-daily administration.

Treatment regimens involving daily injections of existing insulin therapies can be complicated and painful to administer and can result in undesired side effects, such as hypoglycemia and weight gain. Therefore, many diabetic patients are unwilling or unable to comply, or are incapable of complying, with the insulin therapy necessary to maintain close control of blood glucose levels. Poor glycemic control increases a patient's risk for developing serious diabetes-related complications, including heart disease, stroke, nerve damage, lower limb amputation, vision loss, and kidney disease. Research is being conducted to identify insulin products with longer duration of action; thus, requiring fewer injections than currently available insulin products to improve acceptance and compliance.

CN103509118 describes proteins with a human insulin B-chain and human insulin A-chain joined by a 4 to 50 amino acid C-peptide connection sequence, and with the insulin A-chain attached directly, without an additional linker, to an immunoglobulin Fc fragment, and states that testing in mice shows that such proteins have an in vivo half-life as long as about 3 days. KR101324828 describes proinsulin analogs linked to immunoglobulin Fc regions through the use of non-peptidyl linkers, and states that such proteins provide increased serum half-life over existing therapies. The publication states that the non-peptidyl linkers represent an improvement over peptide linkers, asserting that fusion proteins using peptide linkers cannot increase the half-life of an active medication in the blood because peptide linkers are easily severed by enzymes in the body.

Despite the disclosures above, and/or in any other publications, the present inventors overcame multiple obstacles to discover fusion proteins comprising insulin receptor agonists, peptide linkers, and human IgG Fc regions that meet the ongoing need for a glucose-lowering product with increased duration of action, sufficient for less frequent dosing than currently available insulin products, including dosing as infrequently as once-weekly. For example, in order to achieve the desired prolonged time action profile, it was necessary to engineer fusion proteins with attenuated potency to avoid rapid receptor mediated clearance, a major route of insulin clearance, but that still have enough potency to provide sufficient glucose lowering. Further, in order to minimize renal clearance, the other major route of insulin clearance, and to regulate peripheral exposure through hydrodynamic size-limited paracellular diffusion, fusion proteins had to be engineered which were sufficiently large, and which would not have the insulin receptor agonist proteolytically cleaved from the human IgG Fc region after being administered, as such cleavage would result in faster than desired renal clearance of the insulin receptor agonist even if the human IgG Fc region remained in circulation. In addition, IgG Fc domains have evolved to self-associate to form stable dimers, and when such a dimer is formed from two fusion proteins, each comprising an insulin moiety fused with an IgG Fc region, the two insulin moieties are brought into close proximity to one another, enabling self-association, or dimerization, of the insulin moieties, mediated through the insulin B-chain self-association regions. Such insulin dimers are inactive, so fusion proteins with reduced self-association of the insulin receptor agonist moieties had to be engineered. Multiple additional challenges were overcome to create a fusion protein suitable for commercial manufacture and formulation as a therapeutic. The present invention provides fusion proteins which have prolonged duration of action compared to existing insulin treatments, allowing for less frequent injections than existing insulin products, including up to once weekly, thus reducing the complexity of and pain associated with existing treatment regimens involving more frequent injections. The fusion proteins of the present invention have a flat pharmacokinetic profile and restricted peripheral exposure, resulting in low day-to-day variability, and minimal incidence of hypoglycemia, including when provided in combination with an additional diabetes medication, such as an incretin-based therapy. The fusion proteins of the present invention may also provide prolonged duration of action without causing weight gain.

The present invention provides a fusion protein comprising:

a) an insulin receptor agonist having the general formula $Z_1-Z_2-Z_3$, wherein i) $Z_1$ is an insulin B-chain analog, comprising the amino acid sequence:

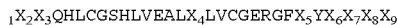

wherein $X_1$ is F, Q or A; $X_2$ is V or G; $X_3$ is N, K, D, G, Q, A or E; $X_4$ is E, Y, Q, or H; $X_5$ is H or F; $X_6$ is G, T, S, H, V or is absent; $X_7$ is G, E, P, K, D, S, H or is absent; $X_8$ is G, E, K, P, Q, D, H or is absent; $X_9$ is G, T, S, E, K, A or is absent, provided that the insulin B-chain analog includes at least one modification from the amino acid sequence of the B-chain of a molecule of human insulin at $X_4$, $X_5$, $X_6$, $X_7$, $X_8$, or $X_9$ (SEQ ID NO:1);

ii) $Z_2$ is a first peptide linker comprising 5 to 10 amino acids, wherein at least 5 of said amino acids are G residues; and iii) $Z_3$ is an insulin A-chain analog comprising the amino acid sequence:

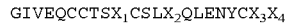

$X_1$ is T or I; $X_2$ is D, Y, Q or E; $X_3$ is G, N, S or A; and $X_4$ is any naturally occurring amino acid, or is absent, provided that if $X_3$ is N, then $X_4$ must be an amino acid other than G or N (SEQ ID NO:2);

b) a second peptide linker; and c) a human IgG Fc region;

wherein the C-terminal residue of the insulin receptor agonist is directly fused to the N-terminal residue of the second peptide linker, and the C-terminal residue of the second peptide linker is directly fused to the N-terminal residue of the IgG Fc region.

The present invention also provides a fusion protein consisting of:

a) an insulin receptor agonist having the general formula $Z_1-Z_2-Z_3$, wherein i) $Z_1$ is an insulin B-chain analog, having the amino acid sequence:

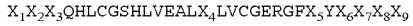

wherein $X_1$ is F, Q or A; $X_2$ is V or G; $X_3$ is N, K, D, G, Q, A or E; $X_4$ is E, Y, Q, or H; $X_5$ is H or F; $X_6$ is G, T, S, H, V or is absent; $X_7$ is G, E, P, K, D, S, H or is absent; $X_8$ is G, E, K, P, Q, D, H or is absent; $X_9$ is G, T, S, E, K, A or is absent, provided that the insulin B-chain analog includes at least one modification from the amino acid sequence of the B-chain of a molecule of human insulin at $X_4$, $X_5$, $X_6$, $X_7$, $X_8$, or $X_9$ (SEQ ID NO:1);

ii) $Z_2$ is a first peptide linker comprising 5 to 10 amino acids, wherein at least 5 of said amino acids are G residues; and iii) $Z_3$ is an insulin A-chain analog having the amino acid sequence:

$X_1$ is T or I; $X_2$ is D, Y, Q or E; $X_3$ is G, N, S or A; and $X_4$ is any naturally occurring amino acid, or is absent, provided that if $X_3$ is N, then $X_4$ must be an amino acid other than G or N (SEQ ID NO:2);

b) a second peptide linker; and c) a human IgG Fc region;

wherein the C-terminal residue of the insulin receptor agonist is directly fused to the N-terminal residue of the second peptide linker, and the C-terminal residue of the second peptide linker is directly fused to the N-terminal residue of the IgG Fc region.

The present invention also provides a pharmaceutical composition comprising a fusion protein of the present invention and at least one pharmaceutically acceptable excipient.

The present invention also provides a method of treating a patient with diabetes mellitus, obesity, dyslipidemia or metabolic syndrome, comprising administering to a patient in need thereof a therapeutically effective amount of a fusion protein of the present invention. The present invention also provides a method of treating or preventing a diabetes-related condition selected from the group consisting of heart disease, stroke, nephropathy, retinopathy, and kidney disease, comprising administering to a patient in need thereof a therapeutically effective amount of a fusion protein of the present invention.

The invention also provides a fusion protein of the present invention for use in therapy.

The present invention also provides the use of a fusion protein of the present invention in the manufacture of a medicament.

The present invention also provides polynucleotides encoding a fusion protein of the present invention.

The present invention also provides a process for producing a fusion protein of the present invention, said process comprising the steps of:

1. culturing a mammalian host cell comprising a polynucleotide encoding a fusion protein of the present invention under conditions such that said fusion protein is expressed; and 2. recovering from said host cell a fusion protein;

The present invention also provides a fusion protein produced by the process described above.

FIG. 1 provides pharmacodynamic data for exemplary fusion proteins of the present invention in a streptozotocin (STZ)-treated rat diabetes model.

FIG. 2 provides a schematic diagram of configurations of proteins described herein. It should be noted that the particular shapes (e.g., ovals, half-circles, etc.) used in the diagrams in FIG. 2 are not intended to describe or characterize, and should not be used to construe, the meaning or structure of the individual components of the fusion proteins of the present invention.

In certain embodiments, the insulin B-chain analog includes at least one modification from the amino acid sequence of the B-chain of a molecule of human insulin at $X_4$ or $X_5$ of SEQ ID NO:1, and at least one modification from the amino acid sequence of the B-chain of a molecule of human insulin at $X_6$, $X_7$, $X_8$, or $X_9$ of SEQ ID NO:1.

In certain embodiments, the insulin B-chain analog includes at least two modifications from the amino acid sequence of the B-chain of a molecule of human insulin at $X_6$, $X_7$, $X_8$, or $X_9$ of SEQ ID NO:1.

In certain embodiments, the insulin B-chain analog includes modifications from the amino acid sequence of the B-chain of a molecule of human insulin at $X_6$, $X_7$, $X_8$, and $X_9$ of SEQ ID NO:1.

In certain embodiments, the insulin B-chain analog has the amino acid sequence of SEQ ID NO: 1 wherein $X_6$-$X_9$ are each G.

In certain embodiments, the insulin B-chain analog includes modifications from the amino acid sequence of the B-chain of a molecule of human insulin at $X_4$ and $X_5$ of SEQ ID NO:1.

In certain embodiments, the insulin B-chain analog has the sequence of SEQ ID NO:1, wherein: $X_1$ is F; $X_2$ is V; $X_3$ is N or D; $X_4$ is E; $X_5$ is H.

In certain embodiments, the insulin B-chain analog includes modification from the amino acid sequence of the B-chain of a molecule of human insulin at each of positions $X_4$, $X_5$, $X_6$, $X_7$, $X_8$, and $X_9$ of SEQ ID NO:1.

In certain embodiments, the insulin B-chain analog comprises the sequence of SEQ ID NO:1, wherein: $X_1$ is F; $X_2$ is V; $X_3$ is N or D; $X_4$ is E; $X_5$ is H; and $X_6$-$X_9$ are each G.

In certain embodiments, the insulin A-chain analog includes at least one modification from the amino acid sequence of the human insulin A-chain at $X_1$ or $X_2$ of SEQ ID NO:2.

In certain embodiments, the insulin A-chain analog includes modifications from the amino acid sequence of the human insulin A-chain at both $X_1$ and $X_2$ of SEQ ID NO:2.

In certain embodiments, the insulin A-chain analog has the sequence of SEQ ID NO:2, wherein: $X_1$ is I or T; $X_2$ is D; $X_3$ is G; and $X_4$ is absent.

In certain embodiments, the insulin A-chain analog has the sequence of SEQ ID NO:2, wherein $X_3$ is N and wherein $X_4$ is an amino acid other than G, N, S, V L or P.

In certain embodiments, the insulin B-chain analog includes at least one modification from the amino acid sequence of the B-chain of a molecule of human insulin at $X_4$ or $X_5$ of SEQ ID NO:1, and at least one modification from the amino acid sequence of the B-chain of a molecule of human insulin at $X_6$, $X_7$, $X_8$, or $X_9$ of SEQ ID NO:1; and the insulin A-chain analog includes at least one modification from the amino acid sequence of the human insulin A-chain at $X_1$ or $X_2$ of SEQ ID NO:2.

In certain embodiments, the insulin B-chain analog includes at least two modifications from the amino acid sequence of the B-chain of a molecule of human insulin at $X_6$, $X_7$, $X_8$, or $X_9$ of SEQ ID NO:1; and the insulin A-chain analog includes at least one modification from the amino acid sequence of the human insulin A-chain at $X_1$ or $X_2$ of SEQ ID NO:2.

In certain embodiments, the insulin B-chain analog includes modifications from the amino acid sequence of the B-chain of a molecule of human insulin at $X_6$, $X_7$, $X_8$, and $X_9$ of SEQ ID NO:1; and the insulin A-chain analog includes at least one modification from the amino acid sequence of the human insulin A-chain at $X_1$ or $X_2$ of SEQ ID NO:2.

In certain embodiments, the insulin B-chain analog has the amino acid sequence of SEQ ID NO:1 wherein $X_6$-$X_9$ are each G; and the insulin A-chain analog includes at least one modification from the amino acid sequence of the human insulin A-chain at $X_1$ or $X_2$ of SEQ ID NO:2.

In certain embodiments, the insulin B-chain analog includes modification from the amino acid sequence of the B-chain of a molecule of human insulin at $X_4$ and $X_5$ of SEQ ID NO:1; and the insulin A-chain analog includes at least one modification from the amino acid sequence of the human insulin A-chain at $X_1$ or $X_2$ of SEQ ID NO:2.

In certain embodiments, the insulin B-chain analog comprises the sequence of SEQ ID NO:1, wherein: $X_1$ is F; $X_2$ is V; $X_3$ is N or D; $X_4$ is E; $X_5$ is H; and the insulin A-chain analog includes at least one modification from the amino acid sequence of the human insulin A-chain at $X_1$ or $X_2$ of SEQ ID NO:2.

In certain embodiments, the insulin B-chain analog includes modification from the amino acid sequence of the B-chain of a molecule of human insulin at each of positions $X_4$, $X_5$, $X_6$, $X_7$, $X_8$, and $X_9$ of SEQ ID NO:1; and the insulin A-chain analog includes at least one modification from the amino acid sequence of the human insulin A-chain at $X_1$ or $X_2$ of SEQ ID NO:2.

In certain embodiments, the insulin B-chain analog has the sequence of SEQ ID NO:1, wherein: $X_1$ is F; $X_2$ is V; $X_3$ is N or D; $X_4$ is E; $X_5$ is H; and $X_6$-$X_9$ are each G; and the insulin A-chain analog includes at least one modification from the amino acid sequence of the human insulin A-chain at $X_1$ or $X_2$ of SEQ ID NO:2.

In certain embodiments, the insulin B-chain analog includes at least one modification from the amino acid sequence of the B-chain of a molecule of human insulin at $X_4$ or $X_5$ of SEQ ID NO:1, and at least one modification from the amino acid sequence of the B-chain of a molecule of human insulin at $X_6$, $X_7$, $X_8$, or $X_9$ of SEQ ID NO:1; and the insulin A-chain analog includes modifications from the amino acid sequence of the human insulin A-chain at both $X_1$ and $X_2$ of SEQ ID NO:2.

In certain embodiments, the insulin B-chain analog includes at least two modifications from the amino acid sequence of the B-chain of a molecule of human insulin at $X_6$, $X_7$, $X_8$, or $X_9$ of SEQ ID NO:1; and the insulin A-chain analog includes modifications from the amino acid sequence of the human insulin A-chain at both $X_1$ and $X_2$ of SEQ ID NO:2.

In certain embodiments, the insulin B-chain analog includes modifications from the amino acid sequence of the B-chain of a molecule of human insulin at $X_6$, $X_7$, $X_8$, and $X_9$ of SEQ ID NO:1; and the insulin A-chain analog includes modifications from the amino acid sequence of the human insulin A-chain at both $X_1$ and $X_2$ of SEQ ID NO:2.

In certain embodiments, the insulin B-chain analog has the amino acid sequence of SEQ ID NO:1 wherein $X_6$-$X_9$ are each G; and the insulin A-chain analog includes modifications from the amino acid sequence of the human insulin A-chain at both $X_1$ and $X_2$ of SEQ ID NO:2.

In certain embodiments, the insulin B-chain analog includes modifications from the amino acid sequence of the B-chain of a molecule of human insulin at $X_4$ and $X_5$ of SEQ ID NO:1; and the insulin A-chain analog includes modifications from the amino acid sequence of the human insulin A-chain at both $X_1$ and $X_2$ of SEQ ID NO:2.

In certain embodiments, the insulin B-chain analog comprises the sequence of SEQ ID NO:1, wherein: $X_1$ is F; $X_2$ is V; $X_3$ is N or D; $X_4$ is E; $X_5$ is H; and the insulin A-chain analog includes modifications from the amino acid sequence of the human insulin A-chain at both $X_1$ and $X_2$ of SEQ ID NO:2.

In certain embodiments, the insulin B-chain analog includes modification from the amino acid sequence of the B-chain of a molecule of human insulin at each of positions $X_4$, $X_5$, $X_6$, $X_7$, $X_8$, and $X_9$ of SEQ ID NO:1; and the insulin A-chain analog includes modifications from the amino acid sequence of the human insulin A-chain at both $X_1$ and $X_2$ of SEQ ID NO:2.

In certain embodiments, the insulin B-chain analog has the sequence of SEQ ID NO:1, wherein: $X_1$ is F; $X_2$ is V; $X_3$ is N or D; $X_4$ is E; $X_5$ is H; and $X_6$-$X_9$ are each G; and the insulin A-chain analog includes modifications from the amino acid sequence of the human insulin A-chain at both $X_1$ and $X_2$ of SEQ ID NO:2.

In certain embodiments, the insulin B-chain analog includes at least one modification from the amino acid sequence of the B-chain of a molecule of human insulin at $X_4$ or $X_5$ of SEQ ID NO:1, and at least one modification from the amino acid sequence of the B-chain of a molecule of human insulin at $X_6$, $X_7$, $X_8$, or $X_9$ of SEQ ID NO:1; and the insulin A-chain analog has the sequence of SEQ ID NO:2, wherein: $X_1$ is I or T; $X_2$ is D; $X_3$ is G; and $X_4$ is absent.

In certain embodiments, the insulin B-chain analog includes at least two modifications from the amino acid sequence of the B-chain of a molecule of human insulin at $X_6$, $X_7$, $X_8$, or $X_9$ of SEQ ID NO:1; and the insulin A-chain analog has the sequence of SEQ ID NO:2, wherein: $X_1$ is I or T; $X_2$ is D; $X_3$ is G; and $X_4$ is absent.

In certain embodiments, the insulin B-chain analog includes modifications from the amino acid sequence of the B-chain of a molecule of human insulin at $X_6$, $X_7$, $X_8$, and $X_9$ of SEQ ID NO:1; and the insulin A-chain analog has the sequence of SEQ ID NO:2, wherein: $X_1$ is I or T; $X_2$ is D; $X_3$ is G; and $X_4$ is absent.

In certain embodiments, the insulin B-chain analog has the amino acid sequence of SEQ ID NO:1 wherein $X_6$-$X_9$ are each G, wherein: $X_1$ is I or T; $X_2$ is D; $X_3$ is G; and $X_4$ is absent.

In certain embodiments, the insulin B-chain analog includes modifications from the amino acid sequence of the B-chain of a molecule of human insulin at $X_4$ and $X_5$ of SEQ ID NO:1; and the insulin A-chain analog has the sequence of SEQ ID NO:2, wherein: $X_1$ is I or T; $X_2$ is D; $X_3$ is G; and $X_4$ is absent.

In certain embodiments, the insulin B-chain analog comprises the sequence of SEQ ID NO:1, wherein: $X_1$ is F; $X_2$ is V; $X_3$ is N or D; $X_4$ is E; $X_5$ is H; and the insulin A-chain analog has the sequence of SEQ ID NO:2, wherein: $X_1$ is I or T; $X_2$ is D; $X_3$ is G; and $X_4$ is absent.

In certain embodiments, the insulin B-chain analog includes modification from the amino acid sequence of the B-chain of a molecule of human insulin at each of positions $X_4$, $X_5$, $X_6$, $X_7$, $X_8$, and $X_9$ of SEQ ID NO:1; and the insulin A-chain analog has the sequence of SEQ ID NO:2, wherein: $X_1$ is I or T; $X_2$ is D; $X_3$ is G; and $X_4$ is absent.

In certain embodiments, the insulin B-chain analog has the sequence of SEQ ID NO:1, wherein: $X_1$ is F; $X_2$ is V; $X_3$ is N or D; $X_4$ is E; $X_5$ is H; and $X_6$-$X_9$ are each G; and the insulin A-chain analog has the sequence of SEQ ID NO:2, wherein: $X_1$ is I or T; $X_2$ is D; $X_3$ is G; and $X_4$ is absent.

In certain embodiments, the first peptide linker ($Z_2$) comprises the amino acid sequence: $X_1GX_2GGGG$, wherein $X_1$ is G or is absent; and $X_2$ is G, S or is absent (SEQ ID NO:3).

In certain embodiments, the insulin receptor agonist, i.e., $Z_1$—$Z_2$—$Z_3$ in the fusion protein described above, comprises the amino acid sequence:

$X_1X_2X_3QHLCGSHLVEALX_4LVCGERGFX_5YX_6X_7X_8X_9X_{10}GX_{11}GG$ $GGGIVEQCCTSX_{12}CSLX_{13}QLENYCX_{14}X_{15}$ wherein $X_1$ is F, Q or A; $X_2$ is V or G; $X_3$ is N, K, D, G, Q, A or E; $X_4$ is E, Y, Q, or H; $X_5$ is H or F; $X_6$ is G, T, S, H, V or is absent; $X_7$ is G, E, P, K, D, S, H or is absent; $X_8$ is G, E, K, P, Q, D, H or is absent; $X_9$ is G, T, S, E, K, A or is absent; $X_{10}$ is G or is absent; $X_{11}$ is G, S or is absent; $X_{12}$ is T or I; $X_{13}$ is D, Y, Q or E; $X_{14}$ is G, N, S or A; and $X_{15}$ is any naturally occurring amino acid, or is absent, provided that at least one of $X_4$, $X_5$, $X_6$, $X_7$, $X_8$, or $X_9$ must be a different amino acid than that found, respectively, at position $B_{16}$, $B_{25}$, $B_{27}$, $B_{28}$, $B_{29}$ or $B_{30}$ of the B-chain of a molecule of human insulin, and further provided that if $X_{14}$ is N, then $X_{15}$ must be an amino acid other than G or N (SEQ ID NO:4).

In certain preferred embodiments, the insulin receptor agonist, i.e., $Z_1$—$Z_2$—$Z_3$ in the fusion protein described above has the following amino acid sequence:

(SEQ ID NO: 5)
FVNQHLCGSHLVEALELVCGERGFHYGGGGGGSGGGGGIVEQCCTSTC

SLDQLENYCG.

In certain embodiments, the second peptide linker is a peptide having between 10 and 25 amino acids, wherein at least 50% of said amino acids are G residues. In certain embodiments, the second peptide linker is a peptide comprising the amino acid sequence $[GGGGX]_n$, wherein X is Q, E or S; and wherein $n$ is 2-5 (SEQ ID NO:26). In certain embodiments, the second peptide linker comprises the amino acid sequence:

$GGGGX_1GGGGX_2GGGGX_3GGGGX_4X_5X_6$ wherein $X_1$ is Q or E; $X_2$ is Q or E; $X_3$ is Q or E; $X_4$ is G, E, Q or is absent; $X_5$ is G or absent; and $X_6$ is G or is absent (SEQ ID NO:6).

In certain preferred embodiments, the second peptide linker has the amino acid sequence:

(SEQ ID NO: 7)
GGGGQGGGGQGGGGQGGGGG.

In certain embodiments, the human IgG Fc region comprises fragments from one heavy chain of an IgG antibody. A schematic diagram of a fusion protein comprising such an IgG region is provided in diagram (A) in FIG. 2. In other embodiments, the human IgG Fc region comprises fragments from two heavy chains of an IgG antibody. A schematic diagram of a fusion protein comprising such an IgG region is provided in diagram (B) in FIG. 2.

In certain embodiments, the human IgG Fc region is an Fc region from an IgG1, IgG2 or IgG4 antibody.

In certain embodiments, the human IgG Fc region is an Fc region from an IgG1 antibody comprising the following amino acid sequence:

$CPPCPAPELLGGPSVX_1LX_2PPKPKDTLMISRTPEVTCX_3VX_4DVSHED$ $PEVKFNWYVDGVEVHNAKTKPREEQYX_5STYRVVSVLTVLHQDWLNGKEY$ $KCKVSNKALPAPIEKTISKAKGQPREPQVYTLPPSRDELTKNQVSLTC$

-continued

LVKGFYPSDIAVEWESNGQPENNYKTTPPVLDSDGSFFLYSKLTVDK

SRWQQGNVFSCSVMHEALHNHYTQKSLSLSPGX$_6$ wherein $X_1$ is F, Q or E; $X_2$ is F, Q or E; $X_3$ is V or T; $X_4$ is V or T; $X_5$ is N, D or Q; and $X_6$ is K or is absent. (SEQ ID NO:8)

In certain embodiments, the IgG Fc region comprises the amino acid sequence of SEQ ID NO:8 and further comprises some or all of the amino acids that would be found in a wild-type IgG1 Fc sequence to the N-terminal side of the C residue at position 1 in SEQ ID NO:8.

Preferably, the human IgG Fc region is from either an IgG2 or IgG4 antibody.

In certain embodiments, the human IgG Fc region is an Fc region from an IgG4 antibody comprising the following amino acid sequence:

PCPPCPAPEAAGGPSVX$_1$LX$_2$PPKPKDTLMISRTPEVTCX$_3$VX$_4$DVSQE

DPEVQFNWYVDGVEVHNAKTKPREEQFX$_5$STYRVVSVLTVLHQDWLNGK

EYKCKVSNKGLPSSIEKTISKAKGQPREPQVYTLPPSQEEMTKNQVSLT

CLVKGFYPSDIAVEWESNGQPENNYKTTPPVLDSDGSFFLYSX$_6$LTVDK

SRWQEGNVFSCSVMHEALHNHYTQKSLSLSLGX$_7$ wherein $X_1$ is F, Q or E; $X_2$ F, Q or E; $X_3$ is V or T; $X_4$ is V or T; $X_5$ is N, D or Q; $X_6$ is R, or K; $X_7$ is K or is absent. (SEQ ID NO:9)

In certain embodiments, the IgG Fc region comprises the amino acid sequence of SEQ ID NO:9, and further comprises some or all of the amino acids that would be found in a wild type IgG4 Fc sequence to the N-terminal side of the C residue at position 1 in SEQ ID NO:9. In certain embodiments, the human IgG Fc region comprises the amino acid sequence of SEQ ID NO:9, wherein $X_1$ is F; $X_2$ is F; $X_3$ is V; $X_4$ is V; $X_5$ is N; $X_6$ is R; and $X_7$ is absent.

In certain embodiments, the human IgG Fc region is an Fc region from an IgG2 antibody having the following amino acid sequence:

ECPPCPAPPVAGPSVX$_1$LX$_2$PPKPKDTLMISRTPEVTCX$_3$VX$_4$DVSHED

PEVQFNWYVDGVEVHNAKTKPREEQFX$_5$STFRVVSVLTVVHQDWLNGK

EYKCKVSNKGLPAPIEKTISKTKGQPREPQVYTLPPSREEMTKNQVSLTC

LVKGFYPSDIAVEWESNGQPENNYKTTPPMLDSDGSFFLYSKLTVDKSR

WQQGNVFSCSVMHEALHNHYTQKSLSLSPGX$_6$ wherein $X_1$ is F, Q or E; $X_2$ is F, Q or E; $X_3$ is V or T; $X_4$ is V or T; $X_5$ is N, D or Q; and $X_6$ is K or is absent. (SEQ ID NO:10)

In certain embodiments, the IgG Fc region comprises the amino acid sequence of SEQ ID NO:10, and further comprises some or all of the amino acids that would be found in a wild type IgG2 Fc sequence to the N-terminal side of the E residue at position 1 in SEQ ID NO:10. In certain embodiments, the human IgG Fc region comprises the amino acid sequence of SEQ ID NO:10, wherein $X_1$ is F; $X_2$ is F; $X_3$ is V; $X_4$ is V; $X_5$ is N; and $X_6$ is absent.

In certain embodiments, the fusion protein comprises the amino acid sequence:

X$_1$X$_2$X$_3$QHLCGSHLVEALX$_4$LVCGERGFX$_5$YX$_6$X$_7$X$_8$X$_9$X$_{10}$GX$_{11}$

GGGGGIVEQCCTSX$_{12}$CSLX$_{13}$QLENYCX$_{14}$X$_{15}$GGGGX$_{16}$GGGGX$_{17}$GG

GGX$_{18}$GGGGX$_{19}$X$_{20}$X$_{21}$X$_{22}$CPPCPAPX$_{23}$X$_{24}$AGX$_{25}$PSVFLFPPKP

KDTLMISRTPEVTCVVVDVSX$_{26}$EDPEVQFNWYVDGVEVHNAKTKPREE

QFNSTX$_{27}$RVVSVLTVX$_{28}$HQDWLNGKEYKCKVSNKGLPX$_{29}$X$_{30}$IEKTI

SKX$_{31}$KGQPREPQVYTLPPSX$_{32}$EEMTKNQVSLTCLVKGFYPSDIAVEWE

SNGQPENNYKTTPPX$_{33}$LDSDGSFFLYSX$_{34}$LTVDKSRWQX$_{35}$GNVFSC

SVMHEALHNHYTQKSLSLSX$_{36}$G wherein $X_1$ is F, Q or A; $X_2$ is V or G; $X_3$ is N, K, D, G, Q, A or E; $X_4$ is E, Y, Q, or H; $X_5$ is H or F; $X_6$ is G, T, S, H, V or is absent; $X_7$ is G, E, P, K, D, S, H or is absent; $X_8$ is G, E, K, P, Q, D, H or is absent; $X_9$ is G, T, S, E, K, A or is absent, provided that at least one of $X_4$, $X_5$, $X_6$, $X_7$, $X_8$, or $X_9$ is an amino acid other than that which is present, respectively, at position $B_{16}$, $B_{25}$, $B_{27}$, $B_{28}$, $B_{29}$ or $B_{30}$ of a human insulin B-chain; $X_{10}$ is G or is absent; $X_{11}$ is G, S or is absent; $X_{12}$ is T or I; $X_{13}$ is D, Y, Q or E; $X_{14}$ is G, N, S or A; $X_{15}$ is any naturally occurring amino acid, or is absent, provided that if $X_{14}$ is N, then $X_{15}$ must be an amino acid other than G or N; $X_{16}$ is Q or E; $X_{17}$ is Q or E; $X_{18}$ is Q or E; $X_{19}$ is G, E, Q or is absent; $X_{20}$ is G or absent; $X_{21}$ is G or is absent; $X_{22}$ is E or P; $X_{23}$ is E or P; $X_{24}$ is A or V; $X_{25}$ is G or is absent; $X_{26}$ is Q or H; $X_{27}$ is Y or F; $X_{28}$ is L or V; $X_{29}$ is S or A; $X_{30}$ is S or P; $X_{31}$ is A or T; $X_{32}$ is Q or R; $X_{33}$ is V or M; $X_{34}$ is R or K; $X_{35}$ is E or Q; and $X_{36}$ is L or P (SEQ ID NO:11).

In certain embodiments, the present invention provides a fusion protein selected from the group consisting of SEQ ID NO:12, SEQ ID NO:16, SEQ ID NO:17, SEQ ID NO:18, SEQ ID NO:19, SEQ ID NO:20, SEQ ID NO:21, SEQ ID NO:22, SEQ ID NO:23, and SEQ ID NO:24.

In a preferred embodiment, the fusion protein has the amino acid sequence:

```
                                                    (SEQ ID NO: 12)
         10        20        30        40        50        60
FVNQHLCGSHLVEALELVCGERGFHYGGGGGSGGGGIVEQCCTSTCSLDQLENYCGGG 70        80        90       100       110       120
GGQGGGGQGGGGQGGGGECPPCPAPPVAGPSVFLFPPKPKDTLMISRTPEVTCVVVDVS 130       140       150       160       170       180
HEDPEVQFNWYVDGVEVHNAKTKPREEQFNSTFRVVSVLTVVHQDWLNGKEYKCKVSNKG
```

```
              190       200       210       220       230       240
      LPAPIEKTISKTKGQPREPQVYTLPPSREEMTKNQVSLTCLVKGFYPSDIAVEWESNGQP 250       260       270       280       290
      ENNYKTTPPMLDSDGSFFLYSKLTVDKSRWQQGNVFSCSVMHEALHNHYTQKSLSLSPG.
```

In certain embodiments, the fusion proteins of the present invention are present in the form of a dimer. A schematic diagram of such a dimer is provided in diagram (C) in FIG. 2. In certain embodiments, the dimer is a homodimer, wherein the amino acid sequences of the two fusion proteins that make the dimer are the same. In certain embodiments, the dimer is a heterodimer, wherein the amino acid sequences of the two fusion proteins that make up the dimer are different.

In certain embodiments, the pharmaceutical composition of the present invention comprises a fusion protein of the present invention, a buffering agent, a surfactant, and an isotonicity agent. In certain embodiments, the buffering agent is citric acid and/or citrate, the surfactant is polysorbate 80, and the isotonicity agent is mannitol. In certain embodiments, the pH of the composition ranges from about 5.5 to about 8.0. In certain embodiments, the pH ranges from about 6.0 to about 7.4. In certain embodiments, the pH ranges from about 6.0 to 6.75.

In certain embodiments, the pharmaceutical composition further comprises an additional active ingredient. In certain embodiments, the additional active ingredient is an incretin-based therapy. In certain preferred embodiments, the incretin-based therapy is a GLP-1R agonist. Preferably, the GLP-1R agonist is dulaglutide.

In certain embodiments, the method of the present invention comprises administration of a therapeutically effective amount of a fusion protein once daily. In preferred embodiments, a therapeutically effective amount of the fusion protein is administered once weekly. In certain embodiments, a therapeutically effective amount of the fusion protein is administered once monthly. In certain embodiments, the present invention provides a method of treating a patient with diabetes mellitus while reducing the risk of hypoglycemia and/or weight gain, comprising administering to the patient a therapeutically effective amount of a fusion protein of the present invention.

The present invention also provides a method of treating a patient with diabetes mellitus, obesity, dyslipidemia, and/or metabolic syndrome, comprising administering a therapeutically effective amount of a fusion protein of the present invention in combination with an additional active ingredient. The fusion protein and additional active ingredient in such embodiments may be administered simultaneously, sequentially or in a single combined formulation. In certain embodiments, the additional active ingredient is an incretin-based therapy. In certain preferred embodiments, the incretin-based therapy is a GLP-1R agonist. Preferably, the GLP-1R agonist is dulaglutide. In certain embodiments, the combination is administered once daily. In certain preferred embodiments, the combination is administered once weekly. In certain embodiments, the combination is administered once monthly.

In certain embodiments, the present invention provides a fusion protein of the present invention for use in treatment of diabetes mellitus, obesity, dyslipidemia or metabolic syndrome. In certain embodiments, the present invention provides a fusion protein of the present invention for use in treating or preventing a diabetes-related condition selected from the group consisting of heart disease, stroke, nephropathy, retinopathy, and kidney disease. In certain embodiments, the present invention provides a fusion protein of the present invention for use in treating a patient with diabetes mellitus while reducing the risk of hypoglycemia and/or weight gain, comprising administering to the patient a fusion protein of the present invention. In certain embodiments, the fusion protein of the present invention is provided for use in simultaneous, separate or sequential combination with another active ingredient. In certain embodiments, the additional active ingredient is an incretin-based therapy. In certain preferred embodiments, the incretin-based therapy is a GLP-1R agonist.

In certain embodiments, the present invention provides the use of a fusion protein of the present invention in the manufacture of a medicament for the treatment of diabetes mellitus, obesity, dyslipidemia or metabolic syndrome. In certain embodiments, the present invention provides the use of a fusion protein of the present invention in the manufacture of a medicament for the treatment or prevention of a diabetes-related condition selected from the group consisting of heart disease, stroke, nephropathy, retinopathy, and kidney disease. In certain embodiments, the present invention provides the use of a fusion protein of the present invention in the manufacture of a medicament for treating diabetes mellitus while reducing the risk of hypoglycemia and/or weight gain, comprising administering to the patient a fusion protein of the present invention. In certain embodiments, the present invention provides the use of a fusion protein of the present invention in the manufacture of a medicament for the treatment of diabetes mellitus, obesity, dyslipidemia or metabolic syndrome, wherein the medicament is to be administered simultaneously, separately or sequentially in combination with another active ingredient.

When used herein, the term "insulin receptor agonist" refers to a protein that binds to and activates the insulin receptor, resulting in a lowering of blood glucose levels and/or suppression of hepatic glucose output, characteristics which can be tested and measured using known techniques, such as those shown in the studies described below.

The insulin receptor agonist portion of the fusion proteins of the present invention includes an analog of an insulin B-chain and an analog of an insulin A-chain. When used herein, the terms "insulin A-chain" and "insulin B-chain" refer to the A and B chains of the human insulin molecule (CAS No. 11061-68-0), whose native wild type sequences are well-known. The human insulin A-chain consists of 21 amino acids, referred to in the art as $A_1$-$A_{21}$, having the following sequence:

```
                                              (SEQ ID NO: 13)
                   GIVEQCCTSICSLYQLENYCN.
```

The human insulin B-chain consists of 30 amino acids, referred to in the art as $B_1$-$B_{30}$, having the following sequence:

```
                                              (SEQ ID NO: 14)
              FVNQHLCGSHLVEALYLVCGERGFFYTPKT.
```

In a molecule of human insulin, the A- and B-chains are joined by two disulfide bonds, CysA7-CysB7 and CysA20-CysB19. The A-chain has an intra-chain disulfide bond at CysA6-CysA11.

To achieve the desired extended time action profile, the insulin receptor agonist of the fusion protein of the present invention must remain in circulation, and be capable of interacting with the insulin receptor, over an extended period of time. In order for the fusion proteins of the present invention to remain in circulation for the desired period of time, elimination of the fusion proteins must be attenuated. The two primary routes of insulin elimination are renal clearance and insulin receptor-mediated clearance. See Iglesias P, et al. *Diabetes Obes. Metab.* 2008; 10:811-823. To minimize renal clearance, a molecule with hydrodynamic size of at least about the size of human serum albumin is needed, and such a hydrodynamic size is provided in the fusions proteins of the present invention by the human IgG Fc region. As for receptor-mediated clearance, the fusion protein cannot be so potent at the insulin receptor that it results in more rapid receptor-mediated clearance than desired, but the fusion protein must be potent enough, however, to provide sufficient glucose control at doses that are commercially feasible. Thus, the potency of the fusion protein must be carefully balanced, and the structure of the fusion protein of the present invention allows it to achieve such a balance.

Insulin molecules have a tendency to self-associate into dimers and hexamers. Numerous roles have been proposed for the evolutionarily-conserved, self-association tendencies of insulin, including: (1) chemical and thermal stabilization of the molecule during intracellular vacuole storage; (2) protection of the monomeric insulin from fibrillation in vivo; (3) substitution for chaperone-assisted stabilization and folding during intracellular expression; and/or (4) essential for secretory trafficking. The active form of insulin, however, is the monomer.

The tendency of insulin molecules to self-associate, and the inactivity of such self-associated molecules, is relevant to the present invention, because human IgG Fc regions also tend to self-associate to form dimers, typically associated covalently through disulfide bonds in the hinge region, and such dimers are formed from the human IgG Fc regions in the fusion proteins of the present invention. As a result of the dimerization of the human IgG Fc regions, the two insulin receptor agonist "arms" are in close proximity to one another, and thereby exist at relatively high local concentration. In the case of human insulin, such close proximity would tend to favor self-association, or dimerization, of the insulin moieties, affecting the activity of the molecules. A schematic diagram of an Fc fusion protein dimer with insulin moiety arms that have become self-associated, or dimerized, is provided in diagram (D) of FIG. 2. The tendency of insulin molecules to self-associate could also lead to self-association, or dimerization, of insulin moieties from more than one Fc fusion protein dimer; a schematic diagram of a dimer of two Fc fusion protein dimers with self-associated, or dimerized, insulin moieties is provided in diagram (E) of FIG. 2. Further, the insulin moieties in more than two Fc fusion protein dimers could also self-associate in such a fashion to form, for example, a trimer comprised of three dimers, or even higher order aggregates comprised of more than three dimers.

The insulin receptor agonist portion of the fusion protein of the present invention, however, has a reduced tendency to self-associate or dimerize, and thus fusion protein dimers comprised of fusion proteins of the present invention tend to favor the structure depicted in diagram (C) of FIG. 2, as opposed to the structures depicted in diagrams (D) and (E) of FIG. 2. Thus, while the present invention provides a dimer of two fusion proteins, the insulin receptor agonist "arm" of each fusion protein in the dimer maintains a predominately monomeric state, as depicted for example in diagram (C) of FIG. 1, and is thus more capable of interacting with the insulin receptor.

In the fusion proteins of the present invention, the analog of the insulin B-chain in the insulin receptor agonist includes one or more modifications to the amino acid sequence of the human insulin B-chain. In particular, in order to reduce the propensity of the insulin receptor agonist portions to self-associate, or dimerize, the insulin B-chain analog includes one or more modifications from the B-chain of a molecule of human insulin at positions $B_{16}$, $B_{25}$ or $B_{27-30}$, which are represented in SEQ ID NO:1 as positions $X_4$, $X_5$ and $X_{6-9}$, respectively. For example: $X_4$ (which corresponds with $B_{16}$ in the B-chain of a human insulin molecule) may be modified to E, Q or H; $X_5$ (which corresponds with $B_{25}$ in the B-chain of a human insulin molecule) may be modified to H; $X_6$ (which corresponds with $B_{27}$ in the B-chain of a human insulin molecule) may be deleted or modified to G, S, H or V; $X_7$ (which corresponds with $B_{28}$ in the B-chain of a human insulin molecule) may be deleted or modified to G, E, K, D, S or H; $X_8$ (which corresponds with $B_{29}$ in the B-chain of a human insulin molecule) may be deleted or modified to G, E, P, Q, D or H; and $X_9$ (which corresponds with $B_{30}$ in the B-chain of a human insulin molecule) may be deleted or modified to G, S, E or K. In addition to reducing the propensity of the insulin receptor agonist portions to self-associate, modifications to positions $B_{16}$ and $B_{25}$ on the insulin B-chain analog—$X_4$ and $X_5$ of SEQ ID NO:1, respectively—may also be made to adjust potency, improve expression, improve chemical and/or physical stability, improve the ease with which the fusion proteins can be formulated with other commonly used excipients and/or to eliminate deamidation. The insulin B-chain analog may also include additional modifications for these reasons. Referring to the variables in SEQ ID NO:1, such additional modifications include the following: modification of $X_1$ (which corresponds with $B_1$ in the B-chain of a human insulin molecule) to Q or A; modification of $X_2$ (which corresponds with $B_2$ in the B-chain of a human insulin molecule) to G; and/or modification of $X_3$ (which corresponds with $B_3$ in the B-chain of a human insulin molecule) to K, D or G.

In certain preferred embodiments, the insulin B-chain analog includes more than one modification to the amino acid sequence of the human insulin B-chain at positions $X_4$, $X_5$ and $X_{6-9}$ of SEQ ID NO:1. In a preferred embodiment, $X_4$ is E and $X_5$ is H. In certain embodiments, the amino acid sequence of $X_6$-$X_9$ of SEQ ID NO:1 is selected from the group consisting of: GGES, GGGS, GGDS, GGEG, GGGG, SSES, SSGS, GGEE, GGGE, GGEK, GGGK, TPGS, TGGS, HGES, GHES, GGHS, GGEH, HGGS, GHGS, GGGH, GGDD, VGES, TEET, TKPT, GGGG, TGGG, TPGG, EPKT, TDKT, TPGS, EGGS, EGES, EEES, EPES, EPEP and GGDD. In preferred embodiments, the sequence of these four amino acids is GGGS, GGGG or TEET. In particularly preferred embodiments, $X_4$ is E, $X_5$ is H and $X_{6-9}$ is GGGG.

It should be noted that, while $X_6$-$X_9$ of SEQ ID NO:1 are described above as comprising the C-terminal end of the insulin B-chain analog ($Z_1$), these amino acids are not critical to the activity of the fusion proteins at the insulin receptor, and thus may alternatively be considered an extension of the first peptide linker ($Z_2$). For example, in the context of SEQ ID NO:4, $X_6$-$X_9$ may be considered either part of the insulin B-chain analog or the first peptide linker in that insulin receptor agonist.

In the fusion proteins of the present invention, the analog of the insulin A-chain in the insulin receptor agonist portion may include one or more modifications to the amino acid sequence of the human insulin A-chain intended to improve chemical and physical stability, adjust potency, and/or enhance expression. Referring to the variables in SEQ ID NO:2, these modifications include the following: modification of $X_1$ (which corresponds with $A_{10}$ in the A-chain of a human insulin molecule) to T; modification of $X_2$ (which corresponds with $A_{14}$ in the A-chain of a human insulin molecule) to D, Q or E; and/or modification of $X_3$ (which corresponds with $A_{21}$ in the A-chain of a human insulin molecule) to G, S or A. In a preferred embodiment, $X_1$ is T, $X_2$ is D, and $X_3$ is G.

Further, in order to avoid deamidation as well as chemical and/or proteolytic cleavage, if the amino acid at position 21 in the analog of the insulin A-chain in the insulin receptor agonist, i.e., $X_3$ in SEQ ID NO:2, is an N—the amino acid that is present at the corresponding position in a molecule of human insulin—it must not be immediately followed at the C-terminal side by certain amino acids, such as a G or an N, or, in certain embodiments, a P, S, V or L. See, e.g., Vlasak J, Ionescu R., MAbs. 2011 May-June; 3(3):253-63. *Fragmentation of Monoclonal Antibodies*. It should be noted that while this requirement is recited in the first fusion protein described above in the context of the options for positions $X_4$ and $X_5$ in SEQ ID NO:2, which pertains to the analog of the insulin A-chain, it is not critical for the non-glycine residue following an asparagine residue at position 21 in the analog of the insulin A-chain to be considered part of the insulin receptor agonist, as opposed to the second peptide linker. For example, in the context of SEQ ID NO:11, the residue corresponding with position 21 in the A-chain analog portion is represented by $X_{14}$, and the following amino acid, $X_{15}$, could either be considered part of the insulin receptor agonist or the second peptide linker.

As described above, in the fusion proteins of the present invention, the C-terminal residue of the insulin B-chain analog is directly fused to the N-terminal residue of a first peptide linker and the C-terminal residue of the first peptide linker is directly fused to the N-terminal residue of the insulin B-chain analog. The first peptide linker must provide sufficient flexibility for the analogs of the insulin A-chain and B-chain to achieve the structure necessary to bind to the insulin receptor, but must not be so long that it unduly interferes with that binding. The length and composition of the first peptide linker may be adjusted in order to adjust the potency and/or expression of the fusion proteins. In some embodiments, the first peptide linker is 5 to 10 amino acids in length, at least 5 of which are G residues. In certain embodiments, the amino acid sequence of the first peptide linker is selected from the group consisting of: GGGGGG, GGGGG, EGGGGG, GEGGGG, GGEGGG, GGGEGG, GGGGEG, GGGGGE, KGGGGG, GKGGGG, GGKGGG, GGGKGG, GGGGKG, GGGGGK, HGGGGG, GHGGGG, GGHGGG, GGGHGG, GGGGHG, GGGGGH, GGGGGA, GGGGGR, SGGGGG, GSGGGG, GGSGGG, GGSGGGK, GGSGGGG and GGSGGG. In certain preferred embodiments, the sequence of the first peptide linker comprises SEQ ID NO:3. Most preferably, the sequence of the first peptide linker is GGSGGGG (SEQ ID NO:15). The insulin receptor agonist portion of the fusion proteins of the present invention also includes the disulfide bonds found in a molecule of human insulin as described above, namely, two disulfide bonds joining the analogs of the insulin A-chain and B-chain at CysA7-CysB7 and CysA20-CysB19, and an intra-chain disulfide bond in the analog of the insulin A-chain at CysA6-CysA11.

As described above, the C-terminal residue of the insulin receptor agonist portion of the fusion proteins of the present invention is fused to the N-terminal residue of a second peptide linker, and the C-terminal residue of the second peptide linker is fused directly to the N-terminal residue of the Fc portion. It is preferred that the second peptide linker be glycine rich, to provide sufficient conformational flexibility. Preferably, the second peptide linker is less than 30 amino acids in length. In certain preferred embodiments, the second peptide linker is between 10 and 25 amino acids in length, with at least 50% of the amino acids being glycine residues. A preferred second peptide linker includes the sequence $(GGGGX)_n$ wherein X is Q, E or S and n=2-5 (SEQ ID NO:26). A more preferred second peptide linker has the amino acid sequence of SEQ ID NO:6. A most preferred second peptide linker has the amino acid sequence GGGGQGGGGQGGGGQGGGGG (SEQ ID NO:7).

As used herein, the term "human IgG Fc region" has the meaning commonly given to the term in the field of immunology. Specifically, this term refers to a human IgG antibody fragment which is obtained by removing the two antigen binding regions (the Fab fragments) from the antibody. In particular, the Fc region includes the CH2 and CH3 constant region domains of the antibody, and may also include some or all of the hinge region.

As described above, in certain embodiments of the fusion protein of the present invention, the human IgG Fc region comprises fragments of the constant region from one heavy chain of an IgG antibody, a schematic depiction of which is provided in diagram (A) of FIG. 2, and in other embodiments, the human IgG Fc region comprises fragments of the constant regions from two heavy chains of an IgG antibody, a schematic depiction of which is provided in diagram (B) of FIG. 2. In this embodiment, the constant regions of the two heavy chains are associated with one another through non-covalent interactions and disulfide bonds.

There are four IgG subclasses (G1, G2, G3, and G4) each of which has different structures and biological functions known as effector functions. These effector functions are generally mediated through interaction with the Fc receptor (FcγR) or by binding complement factor C1q. Binding to FcγR can lead to antibody-dependent cell-mediated cytolysis, whereas binding to complement factors can lead to complement-mediated cell lysis. The structures and properties of the Fc regions of the IgG subclasses are known in the art. The fusion proteins of the present invention may contain Fc regions from any of the IgG subclasses, although G2 and G4 have lower receptor binding and effector function activities than G1 and G3 antibodies, and are thus preferred.

When used herein, the term human IgG Fc region also includes versions of such antibody fragments which have been modified, elongated and/or truncated, for example, to alter properties or characteristics such as the complement and/or Fc receptor binding functions, effector functions, disulfide bond formation, glycosylation, antibody-dependent cell-mediated cytotoxicity (ADCC), manufacturability, and/or stability. For example, the human IgG Fc regions of the fusion proteins of the present invention may be modified to reduce or remove the N-linked glycosylation site, which will reduce C1q binding affinity and cytotoxicity, and which may aid in immunogenicity, affect conformational stability and in vivo clearance rate, and/or modify the effector functions. The human IgG Fc regions of the fusion proteins of the present invention may also have some or all of the hinge region removed in order to simplify disulfide mediated Fc dimerization. Other examples of alterations include phosphorylation, sulfation, acylation, glycosylation, methylation, acetylation, amidation, and/or modifications to enable production of heterodimer molecules. Techniques for modifying the structures and properties of the human IgG Fc regions of the IgG subclasses are known in the art.

Regardless of the final structure of the fusion protein, the human IgG Fc region must serve to prolong the in vivo plasma half-life of the insulin receptor agonist. In preparing heterologous Fc fusion proteins wherein the Fc portion is being utilized for its ability to extend half-life, it is important to minimize any effector function. Furthermore, the fused insulin receptor agonist must remain able to bind to and activate the insulin receptor to result in a lowering of blood glucose levels and/or suppression of hepatic glucose output, characteristics which can be tested and measured using known techniques, such as those shown in the studies described below. A long half-life in the fusion proteins of the present invention can be demonstrated using, for example, the methods described below.

One preferred human IgG Fc region is an IgG4 Fc region modified to further reduce effector function, promote homodimer formation, and having a portion of the hinge deleted, as in SEQ ID NO:9 wherein $X_1$ is F; $X_2$ is F; $X_3$ is V; $X_4$ is V; $X_5$ is N; $X_6$ is R; and $X_7$ is absent.

Another preferred human IgG Fc region is an IgG2 Fc region having a portion of the hinge deleted, as in SEQ ID NO:10 wherein $X_1$ is F; $X_2$ is F; $X_3$ is V; $X_4$ is V; $X_5$ is N; and $X_6$ is absent.

It should be noted that, although the amino acid sequences of the preferred human IgG Fc regions recited above have portions of the hinge regions removed to simplify disulfide mediated dimerization, those hinge regions may be present in certain embodiments. For example, a wild-type IgG2 Fc region includes the six amino acid sequence ERKCCV at its N-terminal end, and although these amino acids are not recited in the IgG2 Fc region sequence set forth in SEQ ID NO:10, it is contemplated that a human IgG Fc region which comprises the amino acid sequence set forth in SEQ ID NO:10 may further comprise some or all of the six amino acid sequence ERKCCV at its N-terminal end. Similarly, a human IgG Fc region which comprises the amino acid sequence set forth in SEQ ID NO:9 may further comprise some or all of the six amino acids found at the N-terminal end of an IgG4 Fc region, namely ESKYGP. Likewise, a human IgG Fc region which comprises the amino acid sequence set forth in SEQ ID NO:8 may further comprise some or all of the ten amino acids found at the N-terminal end of an IgG1 Fc region, namely: EPKSCDKTHT. Moreover, the precise delineation between which amino acid constitutes the C-terminal end of the second peptide linker and which amino acid constitutes the N-terminal end of the human IgG Fc region is not critical to the structure or function of the fusion protein of the present invention. For example, in the context of SEQ ID NO:11, the residues corresponding with positions $X_{19}$-$X_{22}$ could be described as either the C-terminal end of the second peptide linker or an N-terminal extension of the human IgG Fc region.

As described above, the present invention also relates to polynucleotides that encode any of the fusion proteins of the present invention. The polynucleotides encoding the above-described fusion proteins may be in the form of RNA or DNA, which includes cDNA and synthetic DNA, and which may be double-stranded or single-stranded. The coding sequences that encode the proteins of the present invention may vary as a result of the redundancy or degeneracy of the genetic code.

The polynucleotides that encode for the fusion proteins of the present invention may include the following: only the coding sequence for the proteins, the coding sequence for the proteins and additional coding sequence, such as a leader or secretory sequence or a pro-protein sequence; the coding sequence for the proteins and non-coding sequence, such as introns or non-coding sequence 5' and/or 3' of the coding sequence for the proteins. Thus, the term "polynucleotide encoding a protein" encompasses a polynucleotide that may include not only coding sequence for the proteins but also a polynucleotide that includes additional coding and/or non-coding sequence.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers to permit detection of those cells transformed with the desired DNA sequences.

The fusion proteins of the present invention may readily be produced in mammalian cells such as CHO, NSO, HEK293, BHK, or COS cells; in bacterial cells such as *E. coli*, *Bacillus subtilis*, or *Pseudomonas fluorescence*; in insect cells, or in fungal or yeast cells, which are cultured using techniques known in the art. Insect, and yeast or other fungal cells, however, produce non-human N-glycans, so proteins with N-linked glycosylation produced in such cells may cause immunogenic reactions if administered to patients. Production in such cells thus requires elimination of N-linked glycosylation sites and/or genetic engineering of the cells to produce human N-glycans using techniques known in the art. See, e.g., Hamilton S R, et al., *Production of complex human glycoproteins in yeast*, 301 SCIENCE (5637): 1244-6 (August 2003). Production in mammalian cells is preferred, and the preferred mammalian host cell is the CHOK1SV cell line containing a glutamine synthetase (GS) expression system (see U.S. Pat. No. 5,122,464).

The vectors containing the polynucleotide sequences of interest (e.g., the fusion proteins and expression control sequences) can be transferred into the host cell by well-known methods, which vary depending on the type of cellular host. For example, calcium chloride transformation is commonly utilized for prokaryotic cells, whereas calcium phosphate treatment or electroporation may be used for other cellular hosts.

Various methods of protein purification may be employed and such methods are known in the art and described, for example, in Deutscher, *Methods in Enzymology* 182: 83-89 (1990) and Scopes, *Protein Purification: Principles and Practice,* 3rd Edition, Springer, N.Y. (1994).

As described above, the fusion protein of the present invention in certain embodiments is produced as a dimer. In such a dimer, the human IgG Fc regions of the fusion proteins are associated with one another through non-covalent interactions and disulfide bonds. A schematic depiction of such a dimer is provided in diagram (C) of FIG. 2. When the amino acid sequences of the two fusion proteins that make up such a dimer—e.g., Fusion Protein A and Fusion Protein B in the dimer depicted in diagram (C) of FIG. 2—are the same, the dimer is referred to herein as a "homodimer." As noted above, expression of fusion proteins of the present invention in mammalian cells is preferred, and expression in such cells results in homodimers. The fusion proteins in such homodimers are associated through non-covalent interactions and intermolecular disulfide bonds in the Fc portion. For example, the protein produced by a gene which encodes the fusion protein of SEQ ID NO:12 would be a homodimer covalently bonded through inter-chain disulfide bonds, namely C80 to C80 and C83 to C83.

When the amino acid sequences of two fusion proteins that make up a dimer—e.g., Fusion Protein A and Fusion Protein B in diagram (C) of FIG. 2—are different, the dimer is referred to herein as a "heterodimer." Such a heterodimer may be prepared by techniques known in the art. See, e.g, Lewis S M, et al. NAT. BIOTECHNOL. 32(2):191-8 (2014); Carter, J. IMMUNOL. METHODS, 248(1-2):7-15 (2001); Ridgway, J. B. et al. PROTEIN ENG. 9(7):617-2 (1996).

References herein to pharmaceutical compositions comprising a fusion protein include pharmaceutical compositions which contain a homodimer of that fusion protein, and/or which contain a heterodimer, wherein one member of the heterodimer is that fusion protein. Similarly, references herein to methods comprising administering a fusion protein, include methods comprising administering a homodimer of that fusion protein and/or administering a heterodimer, wherein one member of the heterodimer is that fusion protein. Likewise, references to a fusion protein for use in therapy and/or a fusion protein for use in the manufacture of a medicament include a homodimer of that fusion protein, and/or a heterodimer wherein one member of the heterodimer is that fusion protein, for use in therapy and/or in the manufacture of a medicament, The term "treatment" or "treating," as used herein, refers to the management and care of a patient having diabetes or hyperglycemia, or other condition for which insulin administration is indicated for the purpose of combating or alleviating symptoms and complications of those conditions. Treating includes administering fusion proteins of the present invention to prevent or delay the onset of symptoms or complications, alleviating the symptoms or complications, or eliminating the disease, condition, or disorder. The patient to be treated is a mammal, and preferably, a human being.

The term "prevent" or "preventing," as used herein, refers to reducing the risk or incidence of, or eliminating or slowing the progression of, one or more conditions, symptoms, complications or disorders.

The fusion proteins of the present invention can be used to treat subjects with a wide variety of diseases and conditions. Included are subjects with hyperglycemia, insulin-dependent diabetes as well as subjects with non-insulin dependent diabetes, including treatment naïve subjects as well as subjects being treated with oral medications, such as a sulfonylurea, metformin, thiazolidinedione such as pioglitazone, a-glucosidase inhibitor such as acarbose, and/or noninsulin injectables, including incretin-based therapies, such as DPP-4 inhibitors and GLP-1R agonists. The fusion proteins of the present invention may be used to regulate blood glucose in such patients, and may treat conditions or complications that result from insufficient blood glucose control such as retinopathy, neuropathy or kidney disease.

In certain embodiments, the fusion protein of the present invention is administered every day, every other day, twice weekly, thrice weekly, once weekly, twice monthly or once monthly. In preferred embodiments, the duration of action is sufficiently extended to allow for once weekly dosing. Even for such long acting molecules, however, it will be recognized by those of skill in the art that effective glucose control may also be provided by gradually dose accumulating a drug with a long pharmacokinetic profile using a more frequent treatment regimen, such as once-daily. See, e.g., Heise T and Meneghini L F, 20 ENDOCR. PRACT. p 75-83 (2014).

In certain embodiments, the fusion protein of the present invention is administered in combination with an additional active ingredient, such as insulin or an insulin analog, an incretin-based therapy, or an oral diabetes medication, such as a sulfonylurea, metformin, thiazolidinedione such as pioglitazone or an a-glucosidase inhibitor such as acarbose.

The term "incretin-based therapy" includes any treatment which comprises administration of, or promotes, enables, enhances and/or simulates the effects of, a group of metabolic hormones known as incretins, which group includes GLP-1 and gastric inhibitory peptide (GIP). Incretin-based therapies which are currently available include DPP-4 inhibitors and GLP-1R agonists.

A "DPP-4 inhibitor" is a compound that blocks the DPP-4 enzyme, which is responsible for the degradation of incretins. Currently available DPP-4 inhibitors include sitagliptin (Januvia®), and linagliptin (Tradjenta®).

A "GLP-1R agonist" is defined as a compound comprising the amino acid sequence of native human GLP-1 (SEQ ID NO:25), a GLP-1 analog, GLP-1 derivative or GLP-1 fusion protein, which maintains activity at the GLP-1 receptor. GLP-1R activity may be measured by methods known in the art, including using in vivo experiments and in vitro assays that measure GLP-1 receptor binding activity or receptor activation, e.g., assays employing pancreatic islet cells or insulinoma cells, as described in EP 619,322 and U.S. Pat. No. 5,120,712, respectively. A GLP-1 analog is a molecule having a modification including one or more amino acid substitutions, deletions, inversions, or additions when compared with the amino acid sequence of native human GLP-1 (SEQ ID NO:25). A GLP-1 derivative is a molecule having the amino acid sequence of native human GLP-1 (SEQ ID NO:25) or of a GLP-1 analog, but additionally having at least one chemical modification of one or more of its amino acid side groups, a-carbon atoms, terminal amino group, or terminal carboxylic acid group. A GLP-1 fusion protein is a heterologous protein comprising GLP-1, a GLP-1 analog or a GLP-1 derivative portion and a second polypeptide. Currently available GLP-1R agonists include exenatide (Byetta® and Bydureon®), liraglutide (Victoza®), albiglutide (Tanzeum®) and dulaglutide (Trulicity®), the structures of which are known in the art. See, e.g., U.S. Pat. No. 5,424,286 (exenatide); U.S. Pat. No. 6,268,343 (liraglutide); US 2014044717 (albiglutide); and U.S. Pat. No. 7,452,966 (dulaglutide).

In embodiments wherein a fusion protein of the present invention is provided in combination with an additional active ingredient, the fusion protein and additional active ingredient may be administered simultaneously, sequentially or in a single, combined formulation.

The fusion proteins of the present invention are effective in treating such diseases and conditions by administering to a patient in need thereof a therapeutically effective amount of a fusion protein of the present invention. As used herein, the phrase "therapeutically effective amount" refers to that amount of a fusion protein of the present invention sufficient to regulate blood glucose in a patient without causing unacceptable side effects. A therapeutically effective amount of the fusion protein administered to a subject will depend on the type and severity of the disease and on the characteristics of the subject, such as general health, age, sex, body weight, and tolerance to drugs. The skilled artisan will be able to determine appropriate dosages depending on these and other factors. In certain embodiments, a therapeutically effective amount of a fusion protein of the present invention when administered once weekly ranges from about 0.01 nmol/kg to about 100 nmol/kg. More preferably, a therapeutically effective amount of a fusion protein of the present invention when administered once weekly ranges from about 1 nmol/kg to about 50 nmol/kg. More preferably, a therapeutically effective amount of a fusion protein of the present invention when administered once weekly ranges from about 16 nmol/kg to about 25 nmol/kg. In certain embodiments, a therapeutically effective amount of a fusion protein of the present invention when administered once weekly ranges from about 1 mg to about 200 mg. More preferably, a therapeutically effective amount of a fusion protein of the present invention when administered once weekly ranges from about 25 mg to about 175 mg. More preferably, a therapeutically effective amount of a fusion protein of the present invention when administered once weekly ranges from about 100 mg to about 160 mg.

Persons of skill in the art will understand that when the fusion protein of the present invention is administered in combination with another active ingredient, such as a GLP-1R agonist, the dose may be adjusted so that the activity of the two treatments combined is sufficient to regulate blood glucose in a patient. Thus, the amount of fusion protein that must be administered to regulate blood glucose levels in such combinations may be less than would be required if the fusion protein were administered as a monotherapy. For example, when the fusion protein of the present invention is provided in combination with a GLP-1R agonist, the amount of fusion protein to be provided in a once weekly dose may be reduced by up to 50%, as compared to the amount of the same fusion protein for use as a monotherapy, such as the doses described in the preceding paragraph.

Preferably, administration of a therapeutically effective amount of the fusion protein of the present invention in some embodiments will provide effective glucose control while reducing the risk of hypoglycemia and/or weight gain as compared to existing treatments. The incidence of hypoglycemia caused by a diabetes therapy which agonizes the insulin receptor may be minimized by avoiding a rapid spike in the concentration of the therapeutic agent following administration. The fusion proteins of the present invention have an extended time action profile without a rapid spike in concentration following administration.

Moreover, in embodiments wherein the fusion proteins of the present invention are provided in combination with another active ingredient, in particular, a GLP-1R agonist, the hepatopreferential activity of the fusion proteins of the present invention may also reduce the risk of hypoglycemia while controlling glucose levels. Because the fusion protein of the present invention can readily access the liver through the fenestrated sinusoid endothelium, the molecule can control hepatic glucose output, with little, if any, activity at the periphery, while the GLP-1R agonist promotes glucose-dependent secretion of endogenous insulin from the pancreas that is readily capable of perfusing into the periphery to control glucose uptake in muscle and fat.

The fusion proteins of the present invention are administered parenterally, by nasal administration or pulmonary inhalation. Parenteral administration is preferred, and can include, for example, systemic administration, such as by intramuscular, intravenous, subcutaneous, or intraperitoneal injection.

The fusion proteins can be administered to the subject in a pharmaceutical composition, which comprises a fusion protein of the present invention and at least one pharmaceutically acceptable excipient. Such pharmaceutical compositions are typically, though not necessarily, parenteral in nature and may be prepared by any of a variety of techniques using conventional excipients for parenteral products, which are well known in the art. See, e.g., Remington: the Science and Practice of Pharmacy (D. B. Troy, Editor, 21$^{st}$ Edition, Lippincott, Williams & Wilkins, 2006). As described above, the fusion protein of the present invention is a homodimer when expressed in mammalian cells. Thus, when used herein, the term "composition comprising a fusion protein" includes a composition, which contains a homodimer of a fusion protein. In certain embodiments, a pharmaceutical composition of the present invention includes a composition with the fusion protein of the present invention present in a concentration of at least 1 mg/mL, at least 2 mg/mL, at least 5 mg/mL, at least 10 mg/mL, at least 20 mg/mL, at least 25 mg/mL, at least 30 mg/mL, at least 35 mg/mL, at least 50 mg/mL, at least 55 mg/mL, at least 50 mg/mL, at least 65 mg/mL, at least 75 mg/mL, at least 100 mg/mL or greater. In preferred embodiments, the fusion protein is present in a concentration of 10-100 mg/mL. In more preferred embodiments, the fusion protein is present in a concentration of 15-75 mg/mL, and in most preferred embodiments, the fusion protein is present in a concentration of 20-65 mg/mL.

The term "excipient" means any substance added to the composition other than the fusion protein or any other additional active ingredient(s). Examples of such excipients that may be used in the compositions of the present invention include buffering agents, surfactants, isotonicity agents and preservatives.

In certain embodiments, the composition of the present invention includes one or more buffering agents to control the pH of the composition. A "buffering agent" is a substance which resists changes in pH by the action of its acid-base conjugate components. In certain embodiments, the composition of the present invention has a pH from about 5.5 to about 8.0, preferably, between about 6.0 and about 7.4, more preferably between about 6.0 and 6.75. Buffering agents suitable for controlling the pH of the compositions of the present invention in the desired range include, but are not limited to agents such as phosphate, acetate, citrate, or acids thereof, arginine, TRIS, and histidine buffers, as well as combinations thereof. "TRIS" refers to 2-amino-2-hydroxymethyl-1,3,-propanediol, and to any pharmacologically acceptable salt thereof. The free base and the hydrochloride form (i.e., TRIS-HCl) are two common forms of TRIS. TRIS is also known in the art as trimethylol aminomethane, tromethamine, and tris(hydroxymethyl) aminomethane. Preferred buffering agents in the composition of the present invention are citrate, or citric acid, and phosphate.

In certain embodiments, the compositions of the present invention include one or more isotonicity agents to minimize pain upon injection due to cellular swelling or cellular rupture. An "isotonicity agent" is a compound that is physiologically tolerated and imparts a suitable tonicity to a formulation to prevent the net flow of water across cell membranes that are in contact with an administered pharmaceutical composition. Known isotonicity agents include glycerol, salts such as sodium chloride, and monosaccharides including, but not limited to, mannitol, dextrose and lactose. Preferred isotonicity agent(s) are mannitol and sodium chloride.

In certain embodiments, the compositions of the present invention include a surfactant. A "surfactant" is a substance that lowers the surface tension of a liquid. Examples of surfactants used in pharmaceutical compositions and which may be used in certain compositions of the present invention include polysorbate 20, polysorbate 80, polyethylene glycols (e.g., PEG 400, PEG 3000, TRITON X-100), polyethylene glycol alkyl ethers (e.g., BRIJ), polypropylene glycols, block copolymers (e.g., poloxamer, PLURONIC F68; poloxamer 407, PLURONIC F127; TETRONICS), sorbitan alkyl esters (e.g., SPAN), polyethoxylated castor oil (e.g., KOLLIPHOR, CREMOPHOR), and trehalose.

The pharmaceutical compositions of the present invention may also contain a preservative. The term "preservative" refers to a compound added to a pharmaceutical formulation to act as an anti-microbial agent in multi-use and/or titratable compositions. Among preservatives known in the art as being effective and acceptable in parenteral formulations are benzalkonium chloride, benzethonium, chlorohexidine, phenol, m-cresol, benzyl alcohol, methyl- or propyl-paraben, chlorobutanol, o-cresol, p-cresol, chlorocresol, phenylmercuric nitrate, thimerosal, benzoic acid, and various mixtures thereof. Phenolic preservative includes the compounds phenol, m-cresol, o-cresol, p-cresol, chlorocresol, methylparaben, and mixtures thereof. If a preservative is necessary, the preservative used in compositions of the present invention is preferably a phenolic preservative, preferably either m-cresol or phenol.

Certain phenolic preservatives, such as phenol and m-cresol, are known to bind to insulin and insulin hexamers and thereby stabilize a conformational change that increases either physical or chemical stability, or both. In compositions comprising other proteins, however, such preservatives may contribute to the formation of protein aggregates, or high molecular weight polymers (HMWP). See, e.g., Maa Y F and Hsu C C, Int J Pharm 140: 155-168 (1996); Fransson J, et al., Pharm. Res., 14: 606-612 (1997); Lam X M, et al., Pharm. Res., 14: 725-729 (1997); Remmele R L Jr, et al., Pharm Res 15: 200-208. (1998); Thirumangalathu R, et al., J Pharm Sci 95: 1480-1497 (2006). Such protein aggregates in therapeutic formulations are undesirable due to their tendency to induce an immune response.

In certain preferred embodiments, the amino acid sequence of the fusion protein of the present invention is optimized to enhance the physical stability of the fusion protein in compositions which also contain a phenolic preservative. For example, the present inventors surprisingly discovered that the presence of an amino acid mutation at position 10 in the analog of the insulin A-chain (variable $X_1$ in the analog of the insulin A-chain recited in SEQ ID NO:2) reduces the accumulation of aggregates of the fusion protein in the presence of phenolic preservatives, as shown in the stability studies below. The invention is further illustrated by the following examples, which are not to be construed as limiting.

Expression and Purification of Fusion Proteins

Fusion proteins of the present invention are produced in a mammalian cell expression system using the CHO glutamine synthetase (GS) knockout (GSKO) cell line. The GS gene knockout enables tightened selection stringency by eliminating endogenous GS background activity which can allow survival of low- or non-productive cells under selection conditions. Genes coding for fusion proteins are subcloned into the glutamine synthetase (GS) containing expression plasmid. The cDNA sequence encoding the fusion proteins is fused in frame with the coding sequence of a signal peptide which enhances secretion of the fusion protein into the cell culture medium. The expression is driven by the cytomegalovirus (CMV) promoter. CHO GSKO cells are stably transfected using electroporation and the appropriate amount of recombinant expression plasmid.

Transfected cells undergo bulk selection in glutamine-free media. Transfected pools are plated at low density to allow for close-to-clonal outgrowth of stable expressing cells. The masterwells are screened for fusion protein expression and scaled-up in serum-free suspension cultures to be used for production.

Fusion proteins secreted into the media may be purified by Protein A affinity chromatography followed by size exclusion chromatography following standard chromatographic techniques. Briefly, fusion proteins from clarified media are captured by Mab Select Protein A (GE) that has been equilibrated with phosphate buffered saline pH 7.4. Following a wash step with phosphate buffered saline pH 7.4, bound fusion proteins are eluted with 10 mM citric acid pH 3.0. Fractions containing fusion protein are pooled and neutralized by adding 1/10 volume of 1M Tris pH 8.0. Soluble aggregates and multimers may be effectively removed by common techniques, including size exclusion, hydrophobic interaction or ion exchange chromatography. Fractions containing monomeric fusion protein (covalently linked homodimer), as determined by size exclusion chromatography, are pooled, sterile filtered, and stored.

Amino acid sequences of exemplary fusion proteins of the present invention are shown below:

EXAMPLE 1

```
                                              (SEQ ID NO: 12)
         10        20        30        40        50        60
FVNQHLCGSHLVEALELVCGERGFHYGGGGGSGGGGGIVEQCCTSTCSLDQLENYCGGG 70        80        90       100       110       120
GGQGGGGQGGGGQGGGGGECPPCPAPPVAGPSVFLFPPKPKDTLMISRTPEVTCVVVDVS 130       140       150       160       170       180
HEDPEVQFNWYVDGVEVHNAKTKPREEQFNSTFRVVSVLTVVHQDWLNGKEYKCKVSNKG 190       200       210       220       230       240
LPAPIEKTISKTKGQPREPQVYTLPPSREEMTKNQVSLTCLVKGFYPSDIAVEWESNGQP 250       260       270       280       290
ENNYKTTPPMLDSDGSFFLYSKLTVDKSRWQQGNVFSCSVMHEALHNHYTQKSLSLSPG
```

EXAMPLE 2

(SEQ ID NO: 16)

```
         10         20         30         40         50         60
FVNQHLCGSHLVEALYLVCGERGFFYTEETGGGGGGGIVEQCCTSICSLYQLENYCGGGG
         70         80         90        100        110        120
GSGGGGSGGGGSESKYGPPCPPCPAPEAAGGPSVFLFPPKPKDTLMISRTPEVTCVVVDV
        130        140        150        160        170        180
SQEDPEVQFNWYVDGVEVHNAKTKPREEQFNSTYRVVSVLTVLHQDWLNGKEYKCKVSNK
        190        200        210        220        230        240
GLPSSIEKTISKAKGQPREPQVYTLPPSQEEMTKNQVSLTCLVKGFYPSDIAVEWESNGQ
        250        260        270        280        290
PENNYKTTPPVLDSDGSFFLYSRLTVDKSRWQEGNVFSCSVMHEALHNHYTQKSLSLSLG
```

EXAMPLE 3

(SEQ ID NO: 17)

```
         10         20         30         40         50         60
FVNQHLCGSHLVEALELVCGERGFHYGGGGGGSGGGGGIVEQCCTSICSLDQLENYCGGG
         70         80         90        100        110        120
GGQGGGGQGGGGQGGGGQGGPCPPCPAPEAAGGPSVFLFPPKPKDTLMISRTPEVTCVVV
        130        140        150        160        170        180
DVSQEDPEVQFNWYVDGVEVHNAKTKPREEQFNSTYRVVSVLTVLHQDWLNGKEYKCKVS
        190        200        210        220        230        240
NKGLPSSIEKTISKAKGQPREPQVYTLPPSQEEMTKNQVSLTCLVKGFYPSDIAVEWESN
        250        260        270        280        290        300
GQPENNYKTTPPVLDSDGSFFLYSRLTVDKSRWQEGNVFSCSVMHEALHNHYTQKSLSLS
LG
```

EXAMPLE 4

(SEQ ID NO: 18)

```
         10         20         30         40         50         60
FVNQHLCGSHLVEALELVCGERGFHYGGGGGSGGGGGIVEQCCTSICSLDQLENYCGGGG
         70         80         90        100        110        120
GEGGGGEGGGGEGGGGECPPCPAPPVAGPSVFLFPPKPKDTLMISRTPEVTCVVVDVSHE
        130        140        150        160        170        180
DPEVQFNWYVDGVEVHNAKTKPREEQFNSTFRVVSVLTVVHQDWLNGKEYKCKVSNKGLP
        190        200        210        220        230        240
APIEKTISKTKGQPREPQVYTLPPSREEMTKNQVSLTCLVKGFYPSDIAVEWESNGQPEN
        250        260        270        280        290
NYKTTPPMLDSDGSFFLYSKLTVDKSRWQQGNVFSCSVMHEALHNHYTQKSLSLSPG
```

EXAMPLE 5

(SEQ ID NO: 19)

```
         10         20         30         40         50         60
FVNQHLCGSHLVEALELVCGERGFHYGGGGGGSGGGGGIVEQCCTSTCSLDQLENYCGGG
         70         80         90        100        110        120
GGQGGGGQGGGGQGGGGQGGPCPPCPAPEAAGGPSVFLFPPKPKDTLMISRTPEVTCVVV
        130        140        150        160        170        180
DVSQEDPEVQFNWYVDGVEVHNAKTKPREEQFNSTYRVVSVLTVLHQDWLNGKEYKCKVS
        190        200        210        220        230        240
NKGLPSSIEKTISKAKGQPREPQVYTLPPSQEEMTKNQVSLTCLVKGFYPSDIAVEWESN
```

EXAMPLE 6

```
                                        (SEQ ID NO: 20)
         10         20         30         40         50         60
FVGQHLCGSHLVEALELVCGERGFHYGGGGGGSGGGGGIVEQCCTSICSLDQLENYCGGG 70         80         90        100        110        120
GGQGGGGQGGGGQGGGGQGGPCPPCPAPEAAGGPSVFLFPPKPKDTLMISRTPEVTCVVV 130        140        150        160        170        180
DVSQEDPEVQFNWYVDGVEVHNAKTKPREEQFNSTYRVVSVLTVLHQDWLNGKEYKCKVS 190        200        210        220        230        240
NKGLPSSIEKTISKAKGQPREPQVYTLPPSQEEMTKNQVSLTCLVKGFYPSDIAVEWESN 250        260        270        280        290        300
GQPENNYKTTPPVLDSDGSFFLYSRLTVDKSRWQEGNVFSCSVMHEALHNHYTQKSLSLS

LG
```

EXAMPLE 7

```
                                        (SEQ ID NO: 21)
         10         20         30         40         50         60
AGGQHLCGSHLVEALELVCGERGFHYGGGGGSGGGGGIVEQCCTSICSLDQLENYCGGGG 70         80         90        100        110        120
GQGGGGQGGGGQGGGGECPPCPAPPVAGPSVFLFPPKPKDTLMISRTPEVTCVVVDVSHE 130        140        150        160        170        180
DPEVQFNWYVDGVEVHNAKTKPREEQFNSTFRVVSVLTVVHQDWLNGKEYKCKVSNKGLP 190        200        210        220        230        240
APIEKTISKTKGQPREPQVYTLPPSREEMTKNQVSLTCLVKGFYPSDIAVEWESNGQPEN 250        260        270        280        290
NYKTTPPMLDSDGSFFLYSKLTVDKSRWQQGNVFSCSVMHEALHNHYTQKSLSLSPG
```

EXAMPLE 8

```
                                        (SEQ ID NO: 22)
         10         20         30         40         50         60
FVNQHLCGSHLVEALELVCGERGFHYTPKTGGSGGGGGIVEQCCTSTCSLDQLENYCGGG 70         80         90        100        110        120
GGQGGGGQGGGGQGGGGECPPCPAPPVAGPSVFLFPPKPKDTLMISRTPEVTCVVVDVS 70         80         90        100        110        120
HEDPEVQFNWYVDGVEVHNAKTKPREEQFNSTFRVVSVLTVVHQDWLNGKEYKCKVSNKG 70         80         90        100        110        120
LPAPIEKTISKTKGQPREPQVYTLPPSREEMTKNQVSLTCLVKGFYPSDIAVEWESNGQP 70         80         90        100        110        120
ENNYKTTPPMLDSDGSFFLYSKLTVDKSRWQQGNVFSCSVMHEALHNHYTQKSLSLSPG
```

EXAMPLE 9

```
                                        (SEQ ID NO: 23)
         10         20         30         40         50         60
FVNQHLCGSHLVEALELVCGERGFFYTEETGGGGGGGGIVEQCCTSICSLYQLENYCGGGG
```

-continued

```
         70         80         90        100        110        120
GSGGGGSGGGGSGGGGSECPPCPAPPVAGPSVFLFPPKPKDTLMISRTPEVTCVVVDVSH 130        140        150        160        170        180
EDPEVQFNWYVDGVEVHNAKTKPREEQFNSTFRVVSVLTVVHQDWLNGKEYKCKVSNKGL 190        200        210        220        230        240
PAPIEKTISKTKGQPREPQVYTLPPSREEMTKNQVSLTCLVKGFYPSDIAVEWESNGQPE 250        260        270        280        290
NNYKTTPPMLDSDGSFFLYSKLTVDKSRWQQGNVFSCSVMHEALHNHYTQKSLSLSPG
```

EXAMPLE 10

```
                                                  (SEQ ID NO: 24)
         10         20         30         40         50         60
FVGQHLCGSHLVEALELVCGERGFHYGGGGGGSGGGGGIVEQCCTSTCSLDQLENYCGGG 70         80         90        100        110        120
GGQGGGQGGGGQGGGGECPPCPAPPVAGPSVFLFPPKPKDTLMISRTPEVTCVVVDVS 130        140        150        160        170        180
HEDPEVQFNWYVDGVEVHNAKTKPREEQFNSTFRVVSVLTVVHQDWLNGKEYKCKVSNKG 190        200        210        220        230        240
LPAPIEKTISKTKGQPREPQVYTLPPSREEMTKNQVSLTCLVKGFYPSDIAVEWESNGQP 250        260        270        280        290
ENNYKTTPPMLDSDGSFFLYSKLTVDKSRWQQGNVFSCSVMHEALHNHYTQKSLSLSPG
```

In Vitro Activity

Test-lots of Examples 1-3, 5 and 9 are prepared in phosphate buffered saline (PBS, pH 7.4) or 10 mM citrate buffer (pH 6.5) and stored at 4° C. Biosynthetic human insulin (Eli Lilly and Company) is prepared in 0.01 N HCl and stored as frozen aliquots, or prepared in a formulated mixture containing m-cresol, zinc, sodium chloride, and TRIS buffer (pH 7.3) at 100 units/mL and stored at 4° C.

Affinities of fusion proteins are determined in receptor binding assays performed on P1 membranes prepared from stably-transfected 293EBNA cells (293HEK human embryonic kidney cells expressing EBNA-1) over-expressing either human insulin receptor isoform A (hIR-A) or human insulin receptor isoform B (hIR-B) containing a C9 epitope tag at the C-terminus. Binding affinities are determined from a competitive radio-ligand binding assay performed at steady-state using human recombinant (3-[$^{125}$I]-iodotyrosyl-A$^{14}$)-insulin. Values for test samples are calculated as percent relative to the activity of unlabeled human insulin. IC$_{50}$ values are determined from 4-parameter logistic non-linear regression analysis (XLFit version 4.0, IDBS). If necessary, curve top or bottom parameters are set to 100 or 0, respectively.

The affinity constant ($K_i$) is calculated from the IC$_{50}$ value based upon the equation $K_i$=IC$_{50}$/(1+D/K$_d$) where D equals the concentration of radio-ligand used in the experiment and K$_d$ equals the equilibrium binding affinity constant of the radio-ligand for its cognate receptor determined from saturation binding analysis (hIR-A=0.205 nM; hIR-B=0.251 nM). Reported values for K, are shown as geometric mean±the standard error of the mean (SEM), with the number of replicate determinations indicated by "n" (Table 1).

The exemplified fusion proteins have affinity at both hIR-A and hIR-B. Compared to human insulin, the exemplified fusion proteins show reduced binding affinity to hIR-A and hIR-B (Table 1).

TABLE 1

| Sample | Receptor Binding Affinity, Ki, nM (SEM, n) | |
|---|---|---|
|  | hIR-A | hIR-B |
| Example 1 | 24.9 (4.3, n = 10) | 26.2 (4.3, n = 10) |
| Example 2 | 1.61 (0.06, n = 3) | 4.60 (0.86, n = 3) |
| Example 3 | 10.1 (1.5, n = 4) | 14.5 (2.3, n = 4) |
| Example 5 | 35.6 (10.4, n = 4) | 24.6 (3.4, n = 4) |
| Example 9 | 3.74 (1.20, n = 2) | 4.71 (1.78, n = 2) |
| Human insulin | 0.166 (0.008, n = 10) | 0.202 (0.007, n = 10) |

Ki values are geometric means.
SEM is standard error of the mean.
n is the number of observations.

In Vivo Studies

Studies in Streptozotocin (STZ)-Treated Rat Diabetes Model

Effects of Fusion Proteins are investigated in STZ-treated rat diabetes model. Male Sprague-Dawley rats, 400-425 gram body weight, are anesthetized with isoflurane and given a single injection of Zanosar® (STZ item #89256, Teva Parenteral Medicines, 40 mg/kg IV). The rats are used in studies 3 days after injection of Zanosar®; only animals with non-fasted blood glucose between 400-550 mg/dL are used in these studies.

The rats are distributed into groups to provide comparable variance in blood glucose and body weight and then randomized. Blood glucose is measured using Accucheck Aviva glucometer (Roche). STZ-treated rats are given a single subcutaneous (SC) injection of 30 nmol/kg dose.

Blood samples for glucose measurements are collected by tail bleed. Animals have free access to food and water throughout the experiment. Blood glucose data are provided in FIG. 1. Data shown in FIG. 1 are mean±SEM (n=6 for Examples 1 and 8; n=3 for remaining examples). Blood glucose data for time points during the initial feeding period (between 0 and 24 hours) are collected, but are not included in FIG. 1 for ease of visual representation. As shown in FIG. 1, Examples 1-10 each provide glucose lowering for a prolonged period of time.

Pharmacokinetic properties of Examples 1, 3-6 and 9-10 are also characterized following subcutaneous (SC) dosing in STZ-treated rats as described above. Data are generated using an insulin receptor ELISA assay that requires the presence of insulin that is capable of binding the insulin receptor. The insulin receptor ELISA utilizes the human insulin receptor (R&D Systems#1544-IR/CF aa28-944) as capture. The human insulin receptor is attached to an Immunlon 4 HBX plate by mouse anti-6× HisTag antibody (Novagen 70796). Fusion protein standard curve and samples are diluted in 100% rat K3 EDTA plasma and detected by mouse anti-human IgG Fc horseradish peroxidase (SouthernBiotech 9040-05). Concentrations of Examples 3-6 and 9-10 at 336 hour time point are all between 22.1±9.8 mg/mL and 1498±690 mg/mL. Table 3 shows concentrations of Example 1 over time, and Table 4 shows pharmacokinetic parameters following non-compartmental analysis of the data for Example 1. The data support an extended duration of bioavailability for fusion proteins of the present invention.

TABLE 3

| Time (Hours) | Concentration (mg/mL) |
| --- | --- |
| 1 | 335 ± 104 |
| 6 | 3559 ± 447 |
| 12 | 5991 ± 1578 |
| 24 | 10614 ± 1334 |
| 48 | 12629 ± 1811 |
| 96 | 8766 ± 2028 |
| 168 | 5017 ± 253 |
| 240 | 3682 ± 509 |
| 336 | 2014 ± 134 |

Data represent mean and standard deviation of n = 3.

TABLE 4

| PK Parameter | Result |
| --- | --- |
| $AUC_{0-\infty}$ (μg * hr/mL) | 1066 ± 363 |
| $C_{max}$ (μg/mL) | 6.81 ± 1.62 |
| $T_{max}$ (hr) | 40 ± 14 |
| CL or CL/F (mL/hr/kg) | 2.15 ± 0.91 |
| $t_{1/2}$ (hr) | 82 ± 12 |
| % F | 147 |

Data represent mean and standard deviation of n = 3. Abbreviations:
$AUC_{0-\infty}$—area under the curve from 0 to infinity,
$C_{max}$—maximal concentration,
$T_{max}$—time at maximum concentration,
CL—clearance,
F—bioavailability,
t½—half-life.

Euglycemic Clamp Study in Normal Rats

A euglycemic clamp study in male Sprague-Dawley rats is performed to understand overall in vivo activity of Example 1 on glucose utilization and to determine activity of Example 1 in liver versus peripheral tissues. A bolus/continuous infusion of 3-$^3$H-glucose is initiated in chronically catheterized, overnight-fasted rats to determine endogenous glucose production (EGP) under basal conditions. A bolus/continuous intravenous infusion of test article—7 nmol/kg [bolus] and 1 nmol/kg/hr [continuous rate]—or insulin lispro comparator—[no bolus] and 0.75 mU/kg/min [continuous rate]—is then administered and a variable intravenous infusion of 20% glucose is initiated and periodically adjusted to maintain blood glucose concentration at 100-110 mg/dL. Bolus/infusion rates are selected to achieve comparable glucose infusion rates (GIR) and comparable suppression of EGP under euglycemic clamp conditions in each group. Somatostatin is administered to inhibit endogenous insulin secretion. Arterial blood samples are obtained during the experiment to monitor hematocrit, plasma insulin, and free fatty acids, C-peptide, and basal and clamp EGP. At the end of the experiment, 2-[1-$^{14}$C]-deoxyglucose is administered to measure tissue glucose uptake under steady state glucose concentrations. Under these matched conditions, peripheral activity of the test article and comparators is analyzed as glucose uptake in the soleus muscle and suppression of plasma free fatty acids (FFA). All data are analyzed using a one-way Analysis of Variance with Dunnett's post-hoc test using the insulin lispro group as the control comparator.

Bolus and infusion doses of Example 1 result in steady plasma concentration of 274±57 nM over the course of the clamp experiment. As shown in Table 5, both groups of animals achieve comparable GIR during the clamp phase of the experiment. Average blood glucose in the Example 1 group is slightly higher than the insulin lispro group. Both groups have similar basal and clamped EGP rates (Table 5). Furthermore, the percent change from basal EGP in the Example 1 group is comparable to the insulin lispro control group (Table 5). To assess peripheral activity under equivalently clamped conditions, suppression of plasma FFA and muscle glucose uptake are measured. Whereas insulin lispro resulted in a reduction in plasma FFA levels over the course of the clamp experiment, Example 1 did not. (Table 5). In addition, infusion of Example 1 results in a 33% decrease in glucose uptake in the soleus muscle compared to insulin lispro. (Table 5). Collectively, these data indicate Example 1 displays reduced peripheral activity compared to insulin lispro.

TABLE 5

| | Insulin lispro | Example 1 |
| --- | --- | --- |
| Blood Glucose (mg/dL) | 106.3 ± 2.2 | 111.8 ± 1.2* |
| GIR (mg/kg/min) | 4.71 ± 0.46 | 4.72 ± 0.13 |
| EGP Rate (mg/kg/min) Basal | 5.062 ± 0.141 | 5.004 ± 0.093 |
| Clamp | 3.607 ± 0.241 | 3.509 ± 0.160 |
| % Change from Basal EGP | −29.3 ± 3.5 | −30.1 ± 2.5 |
| % Suppression plasma FFA from Basal | −14.5 ± 4.1 | 9.9 ± 2.4* |
| Rg (μmol/100 mg/min) | 11.34 ± 1.73 | 7.66 ± 1.38 |

Values are displayed as mean ± SEM of 13 animals for insulin lispro and 17 animals for Example 1.
Rg = glucose metabolic index. Statistical analysis was completed by one-way ANOVA followed by Dunnett's post-hoc test.
*= Significantly different from insulin lispro ($p < 0.05$).

In Vivo Efficacy in Cynomolgus Monkeys

The pharmacokinetic (PK) parameters of Example 1 are evaluated following a single intravenous dose of 1.5 nmol/kg and a single subcutaneous dose of 3 nmol/kg in cynomolgus monkeys. Plasma samples for the PK analysis are collected from three animals per group/route, over the course of 3 weeks. Two assays are utilized for the PK analysis: insulin receptor ELISA and total IgG Fc ELISA. The insulin receptor ELISA utilizes the human insulin receptor (R&D Systems 1544-IR/CF) as capture. The human insulin receptor is attached to an Immunlon 4 HBX plate by mouse anti-HisTag antibody (Novagen 70796). Example 1 standard curve and samples are diluted in 100% cynomolgus monkey plasma (anticoagulant was K3 EDTA) and detected by mouse anti-human IgG Fc horseradish peroxidase (SouthernBiotech 9040-05). The total IgG ELISA utilizes the anti-human IgG$_2$ (Abcam ab1933) as the capture reagent. Example 1 is diluted in 100% cynomolgus monkey plasma and the detection antibody is the same as in the insulin receptor ELISA. Results from both assays are shown in Table 6, and the associated PK parameters are shown in Table 7. Example 1 shows complete bioavailability in monkeys, and the active insulin assay and the total Fc assay give similar results.

TABLE 6

PK of Example 1 in Normal Cynomolgus Monkeys.

Concentration ± SD (ng/mL)

| | Insulin Receptor ELISA | | Total Fc ELISA | |
|---|---|---|---|---|
| | IV | SC | IV | SC |
| Time (hours) | 1.5 nmol/kg | 3.0 nmol/kg | 1.5 nmol/kg | 3.0 nmol/kg |
| 0.083 | 1213 ± 212 | NA | 2190 ± 1369 | NA |
| 1 | 1172 ± 182 | <43.75 ± NC | 1708 ± 1219 | <43.75 ± NC |
| 3 | 863 ± 114 | 87 ± 25 | 798 ± NC | 92 ± 22 |
| 6 | 726 ± 119 | 272 ± 31 | 688 ± 96 | 209 ± 116 |
| 12 | 576 ± 88 | 579 ± 78 | 457 ± 178 | 409 ± 145 |
| 24 | 422 ± 67 | 788 ± 69 | 332 ± 95 | 685 ± 359 |
| 48 | 299 ± 39 | 805 ± 55 | 260 ± 19 | 802 ± 64 |
| 72 | 219 ± 42 | 651 ± 83 | 199 ± 34 | 770 ± 83 |
| 96 | 173 ± 26 | 544 ± 89 | 159 ± 25 | 703 ± 390 |
| 120 | 146 ± 28 | 452 ± 55 | 152 ± 27 | 574 ± 160 |
| 168 | 83 ± 13 | 289 ± 54 | 126 ± NC | 395 ± 70 |
| 216 | 48 ± NC | 183 ± 44 | 99 ± NC | 208 ± 123 |
| 240 | <43.75 ± NC | 145 ± 25 | 80 ± NC | 242 ± NC |
| 336 | <43.75 ± NC | 63 ± NC | 47 ± NC | NC |
| 504 | <43.75 ± NC | <43.75 ± NC | <43.75 ± NC | <43.75 ± NC |

Data represent mean and standard deviation from n = 3.
Abbreviations:
IV = intravenous;
SD = standard deviation;
NC = not calculated

TABLE 7

PK Parameters derived from Non-compartmental Analysis of Data in Table 6.

| | Insulin Receptor ELISA | | Total Fc ELISA | |
|---|---|---|---|---|
| | IV | SC | IV | SC |
| Dose (nmol/kg) | 1.5 | 3.0 | 1.5 | 3.0 |
| AUC$_{0-inf}$ (µg * hr/mL) | 51.1 ± 6.4 | 127 ± 7 | 62.7 ± 5.8 | 171 ± 17 |
| C$_{max}$ (µg/mL) | 1.22 ± 0.22 | 0.82 ± 0.06 | 2.24 ± 1.38 | 0.90 ± 0.21 |
| T$_{max}$ (hr) | 0 | 48 ± 24 | 0 | 64 ± 28 |
| CL or CL/F (mL/hr/kg) | 1.99 ± 0.24 | 1.59 ± 0.09 | 1.61 ± 0.15 | 1.19 ± 0.11 |
| T$_{1/2}$ (hr) | 61 ± 9 | 70 ± 2 | 127 ± 18 | 148 ± 53 |
| Vss (mL/kg) | 164 ± 31 | NA | 256 ± 47 | NA |
| % F | NA | 125 | NA | 136 |

Data represent mean and standard deviation from n = 3.
Abbreviations:
AUC$_{0-inf}$—area under the curve from 0 to infinity,
C$_{max}$—maximal concentration (for IV administration C$_{max}$ is extrapolated concentration at time 0),
T$_{max}$—time at maximum concentration,
CL—clearance,
F—bioavailability,
t$^{1/2}$—half-life,
V$_{ss}$—steady-state volume of distribution,
NA—not applicable.

Stability

Non-Preserved 65 mg/mL Formulation of Example 1

Example 1 is formulated at 65 mg/mL in 10 mM citrate, 46.4 mg/mL mannitol, 0.02% polysorbate 80, pH 6.5 and stored at 30° C. Samples are analyzed for percent high molecular weight by size exclusion chromatography (SEC) at 0, 2, and 4 weeks by injecting 1 µL of the 65 mg/mL sample. Analytical SEC is performed on an Agilent 1100 system equipped with a TSKgel SuperSW3000 (Tosoh Bioscience) column and 50 mM sodium phosphate, 300 mM NaCl, pH 7.0 mobile phase flowing at 0.4 mL/min for 15 minutes. Peaks are detected at an absorbance of 280 nm and chromatograms are analyzed using ChemStation software. Percent high molecular weight at time zero is 1.13%, at time two weeks is 1.68%, and at time four weeks is 1.74%. These results support stability of Example 1 at 65 mg/mL concentration with minimal growth of soluble aggregate after 4 weeks at 30° C.

Preserved and Non-Preserved 1 mg/mL Formulations of Examples 1 and 3

Examples 1 and 3 are formulated at 1 mg/mL in 10 mM citrate, pH 6.5 in the presence or absence of 30 mM m-Cresol and stored at 30° C. Samples are analyzed for percent high molecular weight by size exclusion chromatography (SEC) at time zero and 2 weeks by injecting 10 µL of the 1 mg/mL sample. Analytical SEC is performed on an Agilent 1100 system equipped with a TSKgel G3000SWxl (Tosoh Bioscience) column and PBS+350 mM NaCl, pH 7.4 mobile phase flowing at 0.5 mL/min for 35 minutes or 45 minutes for samples in the absence or presence of m-cresol, respectively. Peaks are detected at an absorbance of 214 nm and chromatograms are analyzed using ChemStation software. For Example 3, without and with m-cresol, percent high molecular weight at time zero is 0.2% and 3.06%, respectively. Percent high molecular weight at 2 weeks without and with m-cresol was 0.2% and 1.73%, respectively. These results show an immediate increase in soluble aggregate after addition of m-cresol for Example 3 at time zero. For Example 1, in the absence and presence of m-cresol, percent high molecular weight at time zero was 0.16% and 0.15%, respectively. Percent high molecular weight at 2 weeks in the absence and presence of m-cresol was 0.18% and 0.31%, respectively. These results demonstrate stability, in the presence of preservative, of Example 1, which includes modification of the amino acid at position 10 in the analog of the insulin A-chain (variable $X_1$ in SEQ ID NO:2, $Z_3$ in the first fusion protein described above) to a T residue, relative to Example 3, which includes the native I residue at that position, but which otherwise comprises the same insulin receptor agonist amino acid sequence as Example 1.

Sequences

Analog of insulin B-chain
SEQ ID NO: 1
$X_1X_2X_3$QHLCGSHLVEAL$X_4$LVCGERGF$X_5$Y$X_6X_7X_8X_9$ wherein $X_1$ is F, Q or A; $X_2$ is V or G; $X_3$ is N, K, D, G, Q, A or E; $X_4$ is E, Y, Q, or H; $X_5$ is H or F; $X_6$ is G, T, S, H, V or is absent; $X_7$ is G, E, P, K, D, S, H or is absent; $X_8$ is G, E, K, P, Q, D, H or is absent; $X_9$ is G, T, S, E, K, A or is absent, provided that the insulin B-chain analog includes at least one modification from the amino acid sequence of the B-chain of a molecule of human insulin at $X_4$, $X_5$, $X_6$, $X_7$, $X_8$, or $X_9$ Analog of insulin A-chain
SEQ ID NO: 2
GIVEQCCTS$X_1$CSL$X_2$QLENYC$X_3X_4$ $X_1$ is T or I; $X_2$ is D, Y, Q or E; $X_3$ is G, N, S or A; and $X_4$ is any naturally occurring amino acid, or is absent, provided that if $X_3$ is N, then $X_4$ must be an amino acid other than G or N First peptide linker
SEQ ID NO: 3
$X_1$G$X_2$GGGG, wherein $X_1$ is G or is absent; and $X_2$ is G, S or is absent Insulin receptor agonist
SEQ ID NO: 4
$X_1X_2X_3$QHLCGSHLVEAL$X_4$LVCGERGF$X_5$Y$X_6X_7X_8X_9X_{10}$G$X_{11}$GGG

GGIVEQCCTS$X_{12}$CSL$X_{13}$QLENYC$X_{14}X_{15}$ wherein $X_1$ is F, Q or A; $X_2$ is V or G; $X_3$ is N, K, D, G, Q, A or E; $X_4$ is E, Y, Q, or H; $X_5$ is H or F; $X_6$ is G, T, S, H, V or is absent; $X_7$ is G, E, P, K, D, S, H or is absent; $X_8$ is G, E, K, P, Q, D, H or is absent; $X_9$ is G, T, S, E, K, A or is absent; $X_{10}$ is G or is absent; $X_{11}$ is G, S or is absent; $X_{12}$ is T or I; $X_{13}$ is D, Y, Q or E; $X_{14}$ is G, N, S or A; and $X_{15}$ is any naturally occurring amino acid, or is absent, provided that at least one of $X_4$, $X_5$, $X_6$, $X_7$, $X_8$, or $X_9$ must be a different amino acid than that found, respectively, at position $B_{16}$, $B_{25}$, $B_{27}$, $B_{28}$, $B_{29}$ or $B_{30}$ of the B-chain of a molecule of human insulin, and further provided that if $X_{14}$ is N, then $X_{15}$ must be an amino acid other than G or N Insulin receptor agonist
SEQ ID NO: 5
FVNQHLCGSHLVEALELVCGERGFHYGGGGGSGGGGIVEQCCTST

CSLDQLENYCG

Second peptide linker
SEQ ID NO: 6
GGGG$X_1$GGGG$X_2$GGGG$X_3$GGGG$X_4X_5X_6$ wherein $X_1$ is Q or E; $X_2$ is Q or E; $X_3$ is Q or E; $X_4$ is G, E, Q or is absent; $X_5$ is G or absent; and $X_6$ is G or is absent Second peptide linker
SEQ ID NO: 7
GGGGQGGGGQGGGGQGGGG Human IgG Fc region
SEQ ID NO: 8
CPPCPAPELLGGPSV$X_1$L$X_2$PPKPKDTLMISRTPEVTC$X_3$V$X_4$DVSHED

PEVKFNWYVDGVEVHNAKTKPREEQY$X_5$STYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRW

QQGNVFSCSVMHEALHNHYTQKSLSLSPG$X_6$ wherein $X_1$ is F, Q or E; $X_2$ is F, Q or E; $X_3$ is V or T; $X_4$ is V or T; $X_5$ is N, D or Q; and $X_6$ is K or is absent Human IgG Fc region
SEQ ID NO: 9
PCPPCPAPEAAGGPSV$X_1$L$X_2$PPKPKDTLMISRTPEVTC$X_3$V$X_4$DVSQE

DPEVQFNWYVDGVEVHNAKTKPREEQF$X_5$STYRVVSVLTVLHQDWLNGK

EYKCKVSNKGLPSSIEKTISKAKGQPREPQVYTLPPSQEEMTKNQVSLT

CLVKGFYPSDIAVEWESNGQPENNYKTTPPVLDSDGSFFLYS$X_6$LTVDK

SRWQEGNVFSCSVMHEALHNHYTQKSLSLSLG$X_7$ wherein $X_1$ is F, Q or E; $X_2$ F, Q or E; $X_3$ is V or T; $X_4$ is V or T; $X_5$ is N, D or Q; $X_6$ is R, or K; $X_7$ is K or is absent Human IgG Fc region
SEQ ID NO: 10
ECPPCPAPPVAGPSV$X_1$L$X_2$PPKPKDTLMISRTPEVTC$X_3$V$X_4$DVSHEDP

EVQFNWYVDGVEVHNAKTKPREEQF$X_5$STFRVVSVLTVVHQDWLNGKE

YKCKVSNKGLPAPIEKTISKTKGQPREPQVYTLPPSREEMTKNQVSLTC

LVKGFYPSDIAVEWESNGQPENNYKTTPPMLDSDGSFFLYSKLTVDKSR

WQQGNVFSCSVMHEALHNHYTQKSLSLSPG$X_6$ wherein $X_1$ is F, Q or E; $X_2$ is F, Q or E; $X_3$ is V or T; $X_4$ is V or T; $X_5$ is N, D or Q; and $X_6$ is K or absent Fusion protein
SEQ ID NO: 11
$X_1X_2X_3$QHLCGSHLVEAL$X_4$LVCGERGF$X_5X_6X_7X_8X_9X_{10}$G$X_{11}$GGGGG IVEQCCTS$X_{12}$CSL$X_{13}$QLENYC$X_{14}X_{15}$GGGG$X_{16}$GGGG$X_{17}$GGG$X_{18}$

GGGG$X_{19}X_{20}X_{21}X_{22}$CPPCPAP$X_{23}X_{24}$AG$X_{25}$PSVFLFPPKPKDTLM

ISRTPEVTCVVVDVS$X_{26}$EDPEVQFNWYVDGVEVHNAKTKPREEQFN

ST$X_{27}$RVVSVLTV$X_{28}$HQDWLNGKEYKCKVSNKGLP$X_{29}X_{30}$IEKTISK $X_{31}$KGQPREPQVYTLPPS$X_{32}$EEMTKNQVSLTCLVKGFYPSDIAVEWESN

GQPENNYKTTPP$X_{33}$LDSDGSFFLYS$X_{34}$LTVDKSRWQ$X_{35}$GNVFSCS

VMHEALHNHYTQKSLSLS$X_{36}$G wherein $X_1$ is F, Q or A; $X_2$ is V or G; $X_3$ is N, K, D, G, Q, A or E; $X_4$ is E, Y, Q, or H; $X_5$ is H or F; $X_6$ is G, T, S, H, V or is absent; $X_7$ is G, E, P, K, D, S, H or is absent; $X_8$ is G, E, K, P, Q, D, H or is absent; $X_9$ is G, T, S, E, K, A or is absent, provided that at least one of $X_4$, $X_5$, $X_6$, $X_7$, $X_8$, or $X_9$ is an amino acid other than that which is present, respectively, at position $B_{16}$, $B_{25}$, $B_{27}$, $B_{28}$, $B_{29}$ or $B_{30}$ of a human insulin B-chain; $X_{10}$ is G or is absent; $X_{11}$ is G, S or is absent; $X_{12}$ is T or I; $X_{13}$ is D, Y, Q or E; $X_{14}$ is G, N, S or A; $X_{15}$ is any naturally occurring amino acid, or is absent, provided that if $X_{14}$ is N, then $X_{15}$ must be an amino acid other than G or N; $X_{16}$ is Q or E; $X_{17}$ is Q or E; $X_{18}$ is Q or E; $X_{19}$ is G, E, Q or is absent; $X_{20}$ is G or absent; $X_{21}$ is G or is absent; $X_{22}$ is E or P; $X_{23}$ is E or P; $X_{24}$ is A or V; $X_{25}$ is G or is absent; $X_{26}$ is Q or H; $X_{27}$ is Y or F; $X_{28}$ is L or V; $X_{29}$ is S or A; $X_{30}$ is S or P; $X_{31}$ is A or T; $X_{32}$ is Q or R; $X_{33}$ is V or M; $X_{34}$ is R or K; $X_{35}$ is E or Q; and $X_{36}$ is L or P

```
Fusion protein
                                                 SEQ ID NO: 12
        10         20         30         40         50         60
FVNQHLCGSHLVEALELVCGERGFHYGGGGGSGGGGGIVEQCCTSTCSLDQLENYCGGG 70         80         90        100        110        120
GGQGGGGQGGGGQGGGGGECPPCPAPPVAGPSVFLFPPKPKDTLMISRTPEVTCVVVDVS 130        140        150        160        170        180
HEDPEVQFNWYVDGVEVHNAKTKPREEQFNSTFRVVSVLTVVHQDWLNGKEYKCKVSNKG 190        200        210        220        230        240
LPAPIEKTISKTKGQPREPQVYTLPPSREEMTKNQVSLTCLVKGFYPSDIAVEWESNGQP 250        260        270        280        290
ENNYKTTPPMLDSDGSFFLYSKLTVDKSRWQQGNVFSCSVMHEALHNHYTQKSLSLSPG Human insulin A-chain
                                                 SEQ ID NO: 13
GIVEQCCTSICSLYQLENYCN Human insulin B-chain
                                                 SEQ ID NO: 14
FVNQHLCGSHLVEALYLVCGERGFFYTPKT First peptide linker
                                                 SEQ ID NO: 15
GGSGGGG Fusion protein
                                                 SEQ ID NO: 16
        10         20         30         40         50         60
FVNQHLCGSHLVEALYLVCGERGFFYTEETGGGGGGGIVEQCCTSICSLYQLENYCGGGG 70         80         90        100        110        120
GSGGGGSGGGGSESKYGPPCPPCPAPEAAGGPSVFLFPPKPKDTLMISRTPEVTCVVVDV 130        140        150        160        170        180
SQEDPEVQFNWYVDGVEVHNAKTKPREEQFNSTYRVVSVLTVLHQDWLNGKEYKCKVSNK 190        200        210        220        230        240
GLPSSIEKTISKAKGQPREPQVYTLPPSQEEMTKNQVSLTCLVKGFYPSDIAVEWESNGQ 250        260        270        280        290
PENNYKTTPPVLDSDGSFFLYSRLTVDKSRWQEGNVFSCSVMHEALHNHYTQKSLSLSLG Fusion protein
                                                 SEQ ID NO: 17
        10         20         30         40         50         60
FVNQHLCGSHLVEALELVCGERGFHYGGGGGSGGGGGIVEQCCTSICSLDQLENYCGGG 70         80         90        100        110        120
GGQGGGGQGGGGQGGGGQGGPCPPCPAPEAAGGPSVFLFPPKPKDTLMISRTPEVTCVVV 130        140        150        160        170        180
DVSQEDPEVQFNWYVDGVEVHNAKTKPREEQFNSTYRVVSVLTVLHQDWLNGKEYKCKVS 190        200        210        220        230        240
NKGLPSSIEKTISKAKGQPREPQVYTLPPSQEEMTKNQVSLTCLVKGFYPSDIAVEWESN 250        260        270        280        290        300
GQPENNYKTTPPVLDSDGSFFLYSRLTVDKSRWQEGNVFSCSVMHEALHNHYTQKSLSLS

LG

Fusion protein
                                                 SEQ ID NO: 18
        10         20         30         40         50         60
FVNQHLCGSHLVEALELVCGERGFHYGGGGGSGGGGGIVEQCCTSICSLDQLENYCGGGG 70         80         90        100        110        120
GEGGGGEGGGGEGGGGECPPCPAPPVAGPSVFLFPPKPKDTLMISRTPEVTCVVVDVSHE
```

-continued

```
            130       140       150       160       170       180
DPEVQFNWYVDGVEVHNAKTKPREEQFNSTFRVVSVLTVVHQDWLNGKEYKCKVSNKGLP 190       200       210       220       230       240
APIEKTISKTKGQPREPQVYTLPPSREEMTKNQVSLTCLVKGFYPSDIAVEWESNGQPEN 250       260       270       280       290
NYKTTPPMLDSDGSFFLYSKLTVDKSRWQQGNVFSCSVMHEALHNHYTQKSLSLSPG
```

Fusion protein

```
                                                SEQ ID NO: 19
            10        20        30        40        50        60
FVNQHLCGSHLVEALELVCGERGFHYGGGGGSGGGGIVEQCCTSTCSLDQLENYCGGG 70        80        90       100       110       120
GGQGGGGQGGGGQGGGGQGGPCPPCPAPEAAGGPSVFLFPPKPKDTLMISRTPEVTCVVV 130       140       150       160       170       180
DVSQEDPEVQFNWYVDGVEVHNAKTKPREEQFNSTYRVVSVLTVLHQDWLNGKEYKCKVS 190       200       210       220       230       240
NKGLPSSIEKTISKAKGQPREPQVYTLPPSQEEMTKNQVSLTCLVKGFYPSDIAVEWESN 250       260       270       280       290       300
GQPENNYKTTPPVLDSDGSFFLYSRLTVDKSRWQEGNVFSCSVMHEALHNHYTQKSLSLS
LG
```

Fusion protein

```
                                                SEQ ID NO: 20
            10        20        30        40        50        60
FVGQHLCGSHLVEALELVCGERGFHYGGGGGSGGGGIVEQCCTSICSLDQLENYCGGG 70        80        90       100       110       120
GGQGGGGQGGGGQGGGGQGGPCPPCPAPEAAGGPSVFLFPPKPKDTLMISRTPEVTCVVV 130       140       150       160       170       180
DVSQEDPEVQFNWYVDGVEVHNAKTKPREEQFNSTYRVVSVLTVLHQDWLNGKEYKCKVS 190       200       210       220       230       240
NKGLPSSIEKTISKAKGQPREPQVYTLPPSQEEMTKNQVSLTCLVKGFYPSDIAVEWESN 250       260       270       280       290       300
GQPENNYKTTPPVLDSDGSFFLYSRLTVDKSRWQEGNVFSCSVMHEALHNHYTQKSLSLS
LG
```

Fusion protein

```
                                                SEQ ID NO: 21
            10        20        30        40        50        60
AGGQHLCGSHLVEALELVCGERGFHYGGGGGSGGGGIVEQCCTSICSLDQLENYCGGGG 70        80        90       100       110       120
GQGGGGQGGGGQGGGGECPPCPAPPVAGPSVFLFPPKPKDTLMISRTPEVTCVVVDVSHE 130       140       150       160       170       180
DPEVQFNWYVDGVEVHNAKTKPREEQFNSTFRVVSVLTVVHQDWLNGKEYKCKVSNKGLP 190       200       210       220       230       240
APIEKTISKTKGQPREPQVYTLPPSREEMTKNQVSLTCLVKGFYPSDIAVEWESNGQPEN 250       260       270       280       290
NYKTTPPMLDSDGSFFLYSKLTVDKSRWQQGNVFSCSVMHEALHNHYTQKSLSLSPG
```

Fusion protein

```
                                                SEQ ID NO: 22
            10        20        30        40        50        60
FVNQHLCGSHLVEALELVCGERGFHYTPKTGGSGGGGIVEQCCTSTCSLDQLENYCGGG 70        80        90       100       110       120
GGQGGGGQGGGGQGGGGECPPCPAPPVAGPSVFLFPPKPKDTLMISRTPEVTCVVVDVS 130       140       150       160       170       180
HEDPEVQFNWYVDGVEVHNAKTKPREEQFNSTFRVVSVLTVVHQDWLNGKEYKCKVSNKG 190       200       210       220       230       240
LPAPIEKTISKTKGQPREPQVYTLPPSREEMTKNQVSLTCLVKGFYPSDIAVEWESNGQP 250       260       270       280       290
ENNYKTTPPMLDSDGSFFLYSKLTVDKSRWQQGNVFSCSVMHEALHNHYTQKSLSLSPG
```

Fusion protein

SEQ ID NO: 23

```
        10         20         30         40         50         60
FVNQHLCGSHLVEALELVCGERGFFYTEETGGGGGGIVEQCCTSICSLYQLENYCGGGG 70         80         90        100        110        120
GSGGGGSGGGGSGGGGSECPPCPAPPVAGPSVFLFPPKPKDTLMISRTPEVTCVVVDVSH 130        140        150        160        170        180
EDPEVQFNWYVDGVEVHNAKTKPREEQFNSTFRVVSVLTVVHQDWLNGKEYKCKVSNKGL 190        200        210        220        230        240
PAPIEKTISKTKGQPREPQVYTLPPSREEMTKNQVSLTCLVKGFYPSDIAVEWESNGQPE 250        260        270        280        290
NNYKTTPPMLDSDGSFFLYSKLTVDKSRWQQGNVFSCSVMHEALHNHYTQKSLSLSPG
```

Fusion protein

SEQ ID NO: 24

```
        10         20         30         40         50         60
FVGQHLCGSHLVEALELVCGERGFHYGGGGGGSGGGGGIVEQCCTSTCSLDQLENYCGGG 70         80         90        100        110        120
GGQGGGGQGGGGQGGGGGECPPCPAPPVAGPSVFLFPPKPKDTLMISRTPEVTCVVVDVS 130        140        150        160        170        180
HEDPEVQFNWYVDGVEVHNAKTKPREEQFNSTFRVVSVLTVVHQDWLNGKEYKCKVSNKG 190        200        210        220        230        240
LPAPIEKTISKTKGQPREPQVYTLPPSREEMTKNQVSLTCLVKGFYPSDIAVEWESNGQP 250        260        270        280        290
ENNYKTTPPMLDSDGSFFLYSKLTVDKSRWQQGNVFSCSVMHEALHNHYTQKSLSLSPG
```

GLP-1

SEQ ID NO: 25

```
HAEGTFTSDVSSYLEGQAAKEFIAWLVKGRG
```

Second peptide linker (SEQ ID NO: 26)
[GGGGX]$_n$, wherein X is Q, E or S; and wherein n is 2-5.

We claim:

1. A homodimer of two fusion proteins of having the amino acid sequence of SEQ ID NO: 12.

2. A pharmaceutical composition comprising the homodimer of claim 1.

3. A method of treating a patient with diabetes mellitus comprising administering to a patient in need thereof the homodimer of claim 1.

4. A fusion protein having the amino acid sequence of SEQ ID NO: 12.

* * * * *

UNITED STATES PATENT AND TRADEMARK OFFICE
CERTIFICATE OF CORRECTION

PATENT NO. : 9,855,318 B2  
APPLICATION NO. : 15/140519  
DATED : January 2, 2018  
INVENTOR(S) : David Bruce Baldwin et al.

Page 1 of 1

It is certified that error appears in the above-identified patent and that said Letters Patent is hereby corrected as shown below:

In the Claims

Column 79, Line 21, please delete the word "of" from the phrase "proteins of having,"

Signed and Sealed this  
Nineteenth Day of March, 2019

Andrei Iancu  
*Director of the United States Patent and Trademark Office*